(12) United States Patent
Mitelberg et al.

(10) Patent No.: US 9,848,763 B2
(45) Date of Patent: Dec. 26, 2017

(54) ACCESS SYSTEMS AND METHODS OF INTRA-ABDOMINAL SURGERY

(71) Applicant: Apollo Endosurgery, Inc., Austin, TX (US)

(72) Inventors: Vladimir Mitelberg, Austin, TX (US); William Sowers, Austin, TX (US); Brett E. Naglreiter, Hollywood, FL (US); J. Landon Gilkey, Austin, TX (US); Dennis L. McWilliams, Austin, TX (US); Donald K. Jones, Dripping Springs, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 467 days.

(21) Appl. No.: 14/026,116

(22) Filed: Sep. 13, 2013

(65) Prior Publication Data

US 2014/0018618 A1    Jan. 16, 2014

Related U.S. Application Data

(62) Division of application No. 12/121,409, filed on May 15, 2008, now abandoned.

(51) Int. Cl.
*A61B 1/273* (2006.01)
*A61B 1/00* (2006.01)
(Continued)

(52) U.S. Cl.
CPC ........ *A61B 1/2736* (2013.01); *A61B 1/00082* (2013.01); *A61B 1/00135* (2013.01);
(Continued)

(58) Field of Classification Search
CPC .............. A61B 1/0008; A61B 1/00082; A61B 1/00087; A61B 1/00098; A61B 1/00135;
(Continued)

(56) References Cited

U.S. PATENT DOCUMENTS 2,391,792 A    12/1945  Miles et al.
3,039,468 A     6/1962  Price
(Continued)

FOREIGN PATENT DOCUMENTS

WO    WO 02/089655    11/2002
WO    WO 2006/074060    7/2006
WO    WO 2007/127199    11/2007

*Primary Examiner* — Ryan Henderson
(74) *Attorney, Agent, or Firm* — Gordon & Jacobson, P.C.

(57) ABSTRACT

An access system includes a proximal handle, an overtube coupled to the handle, and an endoscope port extending through handle and overtube sized for receiving an endoscope therethrough. The overtube includes anatomic wall securing system that secures a distal portion of the overtube within a hole in the anatomic wall. The overtube is provided with a shaped distal portion or a controllably shapeable distal portion that aids in directing an endoscope inserted through the port to a particular location within the peritoneal cavity. The access system includes a system for insufflating/deflating the peritoneal space separately from the body cavity accessible via a natural orifice. The access system includes a closure system to cinch closed the hole made in the anatomical wall after the access system has been removed from the hole. Methods are provided for inserting the access system through the anatomical wall to perform intra-abdominal surgery.

14 Claims, 30 Drawing Sheets

(51) Int. Cl.
  *A61B 17/32* (2006.01)
  *A61B 1/01* (2006.01)
  *A61B 1/313* (2006.01)
  *A61B 17/3205* (2006.01)
  *A61B 17/34* (2006.01)
  *A61B 17/00* (2006.01)
  *A61B 17/04* (2006.01)

(52) U.S. Cl.
  CPC ............ *A61B 1/00154* (2013.01); *A61B 1/01* (2013.01); *A61B 1/3132* (2013.01); *A61B 17/32056* (2013.01); *A61B 17/3478* (2013.01); *A61B 2017/00278* (2013.01); *A61B 2017/0417* (2013.01); *A61B 2017/0472* (2013.01); *A61B 2017/320044* (2013.01); *A61B 2017/320048* (2013.01); *A61B 2017/320056* (2013.01); *A61B 2017/3425* (2013.01); *A61B 2017/3488* (2013.01)

(58) Field of Classification Search
  CPC ............ A61B 1/00142; A61B 1/00154; A61B 1/005; A61B 1/0051; A61B 1/0058; A61B 1/008; A61B 1/01; A61B 1/012; A61B 1/018; A61B 1/273; A61B 1/2733; A61B 1/2736; A61B 1/31; A61B 2017/00292; A61B 2017/00296; A61B 2017/0034; A61B 2017/00283; A61B 2017/00269; A61B 2017/00278; A61B 2017/3488; A61B 2017/320044; A61B 17/00234; A61M 29/00; A61M 29/02
  USPC ................ 600/104, 106, 114–116, 121–125; 604/164.01–164.12; 606/108, 167, 606/191–192; 128/898
  See application file for complete search history.

(56) References Cited

U.S. PATENT DOCUMENTS

| | | |
|---|---|---|
| 3,910,279 A | 10/1975 | Okada et al. |
| 3,952,742 A | 4/1976 | Taylor |
| 3,980,861 A | 9/1976 | Fukunaga |
| 4,066,070 A | 1/1978 | Utsugi |
| 4,176,662 A | 12/1979 | Frazer |
| 4,222,380 A | 9/1980 | Terayama |
| 4,271,839 A | 6/1981 | Fogarty et al. |
| 4,332,242 A | 6/1982 | Chikama |
| 4,418,692 A | 12/1983 | Guay |
| 4,445,892 A | 5/1984 | Hussein et al. |
| 4,630,609 A | 12/1986 | Chin |
| 4,655,219 A | 4/1987 | Petruzzi |
| 4,762,453 A | 8/1988 | DeCaro |
| 4,770,188 A | 9/1988 | Chikama |
| 4,779,611 A | 10/1988 | Grooters et al. |
| 4,819,633 A | 4/1989 | Bauer et al. |
| 4,887,598 A | 12/1989 | Berke |
| 4,907,591 A | 3/1990 | Vasconcellos et al. |
| 4,917,554 A | 4/1990 | Bronn |
| 5,009,659 A | 4/1991 | Hamlin et al. |
| 5,014,708 A | 5/1991 | Hayashi et al. |
| 5,078,716 A | 1/1992 | Doll |
| 5,080,660 A | 1/1992 | Buelna |
| 5,135,484 A | 8/1992 | Wright |
| 5,150,717 A | 9/1992 | Rosen et al. |
| 5,158,543 A | 10/1992 | Lazarus |
| 5,159,925 A | 11/1992 | Neuwirth et al. |
| 5,188,596 A | 2/1993 | Condon et al. |
| 5,195,507 A | 3/1993 | Bilweis |
| 5,196,024 A | 3/1993 | Barath |
| 5,226,908 A | 7/1993 | Yoon |
| 5,251,611 A | 10/1993 | Zehel et al. |
| 5,275,608 A | 1/1994 | Forman et al. |
| 5,290,284 A | 3/1994 | Adair |
| 5,297,536 A | 3/1994 | Wilk |
| 5,300,023 A | 4/1994 | Lowery et al. |
| 5,308,327 A | 5/1994 | Heaven et al. |
| 5,312,360 A | 5/1994 | Behl |
| 5,318,543 A | 6/1994 | Ross et al. |
| 5,318,564 A | 6/1994 | Eggers |
| 5,334,207 A | 8/1994 | Gay |
| 5,339,799 A | 8/1994 | Kami et al. |
| 5,370,134 A | 12/1994 | Chin et al. |
| 5,372,601 A | 12/1994 | Lary |
| 5,383,889 A | 1/1995 | Warner et al. |
| 5,395,312 A | 3/1995 | Desai |
| 5,400,770 A | 3/1995 | Nakao et al. |
| 5,400,773 A * | 3/1995 | Zhu et al. ..................... 600/207 |
| 5,417,697 A | 5/1995 | Wilk et al. |
| 5,431,173 A | 7/1995 | Chin et al. |
| 5,458,131 A | 10/1995 | Wilk |
| 5,458,583 A | 10/1995 | McNeely et al. |
| 5,507,744 A | 4/1996 | Tay et al. |
| 5,507,765 A | 4/1996 | Mott |
| 5,507,795 A | 4/1996 | Chiang et al. |
| 5,527,273 A | 6/1996 | Manna et al. |
| 5,531,699 A | 7/1996 | Tomba et al. |
| 5,556,405 A | 9/1996 | Lary |
| 5,570,700 A | 11/1996 | Vogeler |
| 5,571,130 A | 11/1996 | Simpson et al. |
| 5,582,609 A | 12/1996 | Swanson et al. |
| 5,588,951 A | 12/1996 | Zhu et al. |
| 5,591,183 A | 1/1997 | Chin |
| 5,599,294 A | 2/1997 | Edwards et al. |
| 5,599,300 A | 2/1997 | Weaver et al. |
| 5,628,753 A | 5/1997 | Cracauer et al. |
| 5,632,746 A | 5/1997 | Middleman et al. |
| 5,643,305 A | 7/1997 | Al-Tameem |
| 5,651,788 A | 7/1997 | Fleischer et al. |
| 5,697,944 A | 12/1997 | Lary |
| 5,702,438 A | 12/1997 | Avitall |
| 5,709,224 A | 1/1998 | Behl et al. |
| 5,713,364 A | 2/1998 | DeBaryshe et al. |
| 5,718,703 A | 2/1998 | Chin |
| 5,728,063 A | 3/1998 | Preissman et al. |
| 5,728,116 A | 3/1998 | Rosenman |
| 5,738,683 A | 4/1998 | Osypka |
| 5,782,747 A | 7/1998 | Zimmon |
| 5,782,800 A | 7/1998 | Yoon |
| 5,800,449 A | 9/1998 | Wales |
| 5,810,882 A | 9/1998 | Bolduc et al. |
| 5,823,947 A | 10/1998 | Yoon et al. |
| 5,827,242 A | 10/1998 | Follmer et al. |
| 5,827,268 A | 10/1998 | Laufer |
| 5,836,947 A | 11/1998 | Fleischman et al. |
| 5,865,816 A | 2/1999 | Quinn |
| 5,868,767 A | 2/1999 | Farley et al. |
| 5,871,475 A | 2/1999 | Frassica |
| 5,885,278 A | 3/1999 | Fleischman |
| 5,887,594 A | 3/1999 | LoCicero, III |
| 5,891,141 A | 4/1999 | Rydell |
| 5,904,696 A | 5/1999 | Rosenman |
| 5,913,870 A | 6/1999 | DeFonzo et al. |
| 5,961,526 A | 10/1999 | Chu et al. |
| 5,984,939 A | 11/1999 | Yoon |
| 5,997,536 A | 12/1999 | Osswald et al. |
| 6,016,452 A | 1/2000 | Kasevich |
| 6,030,365 A | 2/2000 | Laufer |
| 6,032,077 A | 2/2000 | Pomeranz |
| 6,045,570 A | 4/2000 | Epstein et al. |
| 6,056,763 A | 5/2000 | Parsons |
| 6,066,090 A | 5/2000 | Yoon |
| 6,071,283 A | 6/2000 | Nardella et al. |
| 6,098,629 A | 8/2000 | Johnson et al. |
| 6,099,518 A | 8/2000 | Adams et al. |
| 6,110,143 A | 8/2000 | Kamen |
| 6,117,101 A | 9/2000 | Diederich et al. |
| 6,117,148 A | 9/2000 | Ravo et al. |
| 6,132,428 A | 10/2000 | VanDusseldorp |
| 6,132,438 A | 10/2000 | Fleischman et al. |
| 6,146,401 A | 11/2000 | Yoon et al. |
| 6,152,920 A | 11/2000 | Thompson et al. |
| 6,171,319 B1 | 1/2001 | Nobles et al. |

(56) References Cited

U.S. PATENT DOCUMENTS

| | | |
|---|---|---|
| 6,190,382 B1 | 2/2001 | Ormsby et al. |
| 6,190,384 B1 | 2/2001 | Ouchi |
| 6,193,129 B1 | 2/2001 | Bittner et al. |
| 6,258,086 B1 | 7/2001 | Ashley et al. |
| 6,258,119 B1 | 7/2001 | Hussein et al. |
| 6,261,304 B1 | 7/2001 | Hall et al. |
| 6,270,501 B1 | 8/2001 | Freiberg et al. |
| 6,276,883 B1 | 8/2001 | Unsworth et al. |
| 6,279,809 B1 | 8/2001 | Nicolo |
| 6,319,230 B1 | 11/2001 | Palasis et al. |
| 6,324,418 B1 | 11/2001 | Crowley et al. |
| 6,346,099 B1 | 2/2002 | Altman |
| 6,354,297 B1 | 3/2002 | Eiseman |
| 6,358,262 B1 | 3/2002 | Chan et al. |
| 6,423,062 B2 | 7/2002 | Enayati |
| 6,440,061 B1 | 8/2002 | Wenner et al. |
| 6,454,727 B1 | 9/2002 | Burbank et al. |
| 6,461,294 B1 | 10/2002 | Oneda et al. |
| 6,475,184 B1 | 11/2002 | Wang et al. |
| 6,475,226 B1 | 11/2002 | Belef et al. |
| 6,478,794 B1 | 11/2002 | Trapp et al. |
| 6,494,881 B1 | 12/2002 | Bales et al. |
| 6,524,283 B1 | 2/2003 | Hopper et al. |
| 6,535,764 B2 | 3/2003 | Imran et al. |
| 6,572,615 B2 | 6/2003 | Schuyze et al. |
| 6,572,629 B2 | 6/2003 | Kalloo et al. |
| 6,592,608 B2 | 7/2003 | Fisher et al. |
| 6,613,059 B2 | 9/2003 | Schaller et al. |
| 6,623,494 B1 | 9/2003 | Blatter |
| 6,626,921 B2 | 9/2003 | Blatter et al. |
| 6,632,231 B2 | 10/2003 | Radisch, Jr. |
| 6,645,200 B1 | 11/2003 | Koblish et al. |
| 6,660,003 B1 | 12/2003 | DeVore et al. |
| 6,663,589 B1 | 12/2003 | Halevy |
| 6,663,633 B1 | 12/2003 | Pierson, III |
| 6,689,130 B2 | 2/2004 | Arai et al. |
| 6,695,810 B2 | 2/2004 | Peacock, III et al. |
| 6,712,775 B2 | 3/2004 | Burbank et al. |
| 6,736,822 B2 | 5/2004 | McClellan et al. |
| 6,736,828 B1 | 5/2004 | Adams et al. |
| 6,743,244 B2 | 6/2004 | Blatter et al. |
| 6,761,685 B2 | 7/2004 | Adams et al. |
| 6,764,497 B2 | 7/2004 | Fogarty et al. |
| 6,770,026 B2 | 8/2004 | Kan et al. |
| 6,783,491 B2 | 8/2004 | Saadat et al. |
| 6,790,173 B2 | 9/2004 | Saadat et al. |
| 6,796,963 B2 | 9/2004 | Carpenter et al. |
| 6,824,548 B2 | 11/2004 | Smith et al. |
| 6,837,846 B2 | 1/2005 | Jaffe et al. |
| 6,852,091 B2 | 2/2005 | Edwards et al. |
| 6,852,111 B1 | 2/2005 | Lieber |
| 6,860,892 B1 | 3/2005 | Tanaka et al. |
| 6,866,676 B2 | 3/2005 | Kieturakis et al. |
| 6,893,439 B2 | 5/2005 | Fleischman |
| 6,899,721 B2 | 5/2005 | Sferco |
| 6,918,871 B2 | 7/2005 | Schulze |
| 6,921,361 B2 | 7/2005 | Suzuki et al. |
| 6,932,833 B1 | 8/2005 | Sandoval et al. |
| 6,936,014 B2 | 8/2005 | Vetter et al. |
| 6,936,024 B1 | 8/2005 | Houser |
| 6,949,099 B2 | 9/2005 | Shiro et al. |
| 6,951,566 B2 | 10/2005 | Lary |
| 6,960,217 B2 | 11/2005 | Bolduc |
| 6,960,221 B2 | 11/2005 | Ho et al. |
| 6,964,652 B2 | 11/2005 | Guiles et al. |
| 6,964,660 B2 | 11/2005 | Maguire et al. |
| 6,971,989 B2 | 12/2005 | Yossepowitch |
| 6,994,705 B2 | 2/2006 | Nobis et al. |
| 7,029,471 B2 | 4/2006 | Thompson et al. |
| 7,063,682 B1 | 6/2006 | Whayne et al. |
| 7,063,712 B2 | 6/2006 | Vargas et al. |
| 7,089,045 B2 | 8/2006 | Fuimaono et al. |
| 7,252,665 B2 | 8/2007 | Starkebaum |
| 7,776,057 B2 | 8/2010 | Laufer et al. |
| 2001/0009985 A1 | 7/2001 | Durgin et al. |
| 2001/0047177 A1 | 11/2001 | Kasten |
| 2001/0049497 A1 | 12/2001 | Kalloo et al. |
| 2001/0053909 A1 | 12/2001 | Nakada |
| 2002/0022851 A1 | 2/2002 | Kalloo et al. |
| 2002/0055742 A1 | 5/2002 | Lieberman |
| 2002/0055757 A1 | 5/2002 | Torre et al. |
| 2002/0077642 A1 | 6/2002 | Patel et al. |
| 2002/0087170 A1 | 7/2002 | Kuhns et al. |
| 2002/0139379 A1 | 10/2002 | Edwards et al. |
| 2002/0165589 A1 | 11/2002 | Imran et al. |
| 2003/0032143 A1 | 2/2003 | Neff et al. |
| 2003/0045811 A1 | 3/2003 | Hinchliffe et al. |
| 2003/0167071 A1 | 9/2003 | Martin et al. |
| 2003/0181901 A1 | 9/2003 | Maguire et al. |
| 2003/0208211 A1 | 11/2003 | Kortenbach |
| 2003/0216613 A1 | 11/2003 | Suzuki et al. |
| 2003/0229296 A1 | 12/2003 | Ishikawa et al. |
| 2004/0092937 A1 | 5/2004 | Criscuolo et al. |
| 2004/0092970 A1 | 5/2004 | Xavier |
| 2004/0127916 A1 | 7/2004 | Bolduc et al. |
| 2004/0148034 A1 | 7/2004 | Kagan et al. |
| 2004/0193186 A1 | 9/2004 | Kortenbach et al. |
| 2004/0225183 A1 | 11/2004 | Michlitsch et al. |
| 2004/0236316 A1 | 11/2004 | Danitz et al. |
| 2004/0249367 A1 | 12/2004 | Saadat et al. |
| 2004/0249395 A1 | 12/2004 | Mikkaichi et al. |
| 2004/0254572 A1 | 12/2004 | McIntyre et al. |
| 2005/0038462 A1 | 2/2005 | Lubock et al. |
| 2005/0049460 A1 | 3/2005 | Mikkaichi et al. |
| 2005/0101837 A1 | 5/2005 | Kalloo et al. |
| 2005/0149099 A1 | 7/2005 | Yamano et al. |
| 2005/0209653 A1 | 9/2005 | Herbert et al. |
| 2005/0222567 A1 | 10/2005 | Ouchi |
| 2005/0234294 A1 | 10/2005 | Saadat et al. |
| 2005/0247320 A1 | 11/2005 | Stack et al. |
| 2005/0261708 A1 | 11/2005 | Pasricha |
| 2005/0272977 A1 | 12/2005 | Saadat et al. |
| 2005/0273138 A1 | 12/2005 | To et al. |
| 2005/0277942 A1 | 12/2005 | Kullas et al. |
| 2005/0277945 A1 | 12/2005 | Saadat et al. |
| 2005/0288691 A1 | 12/2005 | Lieboff |
| 2006/0004409 A1 | 1/2006 | Nobis et al. |
| 2006/0004410 A1 | 1/2006 | Nobis et al. |
| 2006/0095079 A1 | 5/2006 | Gerber |
| 2006/0100614 A1 | 5/2006 | Long |
| 2006/0129154 A1 | 6/2006 | Shipp |
| 2006/0184048 A1 | 8/2006 | Saadat |
| 2006/0189889 A1 | 8/2006 | Gertner |
| 2006/0237023 A1* | 10/2006 | Cox ................ A61B 17/0057 128/898 |
| 2007/0043255 A1 | 2/2007 | O'Donnell |
| 2007/0055206 A1 | 3/2007 | To et al. |
| 2007/0100375 A1 | 5/2007 | Mikkaichi et al. |
| 2007/0161855 A1 | 7/2007 | Mikkaichi et al. |
| 2007/0203517 A1* | 8/2007 | Williams et al. ............ 606/191 |
| 2008/0045803 A1* | 2/2008 | Williams ........... A61B 1/00052 600/204 |
| 2008/0262302 A1* | 10/2008 | Azarbarzin et al. .......... 600/114 |
| 2009/0018592 A1 | 1/2009 | Pitbladdo |
| 2009/0124999 A1 | 5/2009 | Horton et al. |
| 2010/0261962 A1* | 10/2010 | Friedberg .................... 600/114 |

* cited by examiner

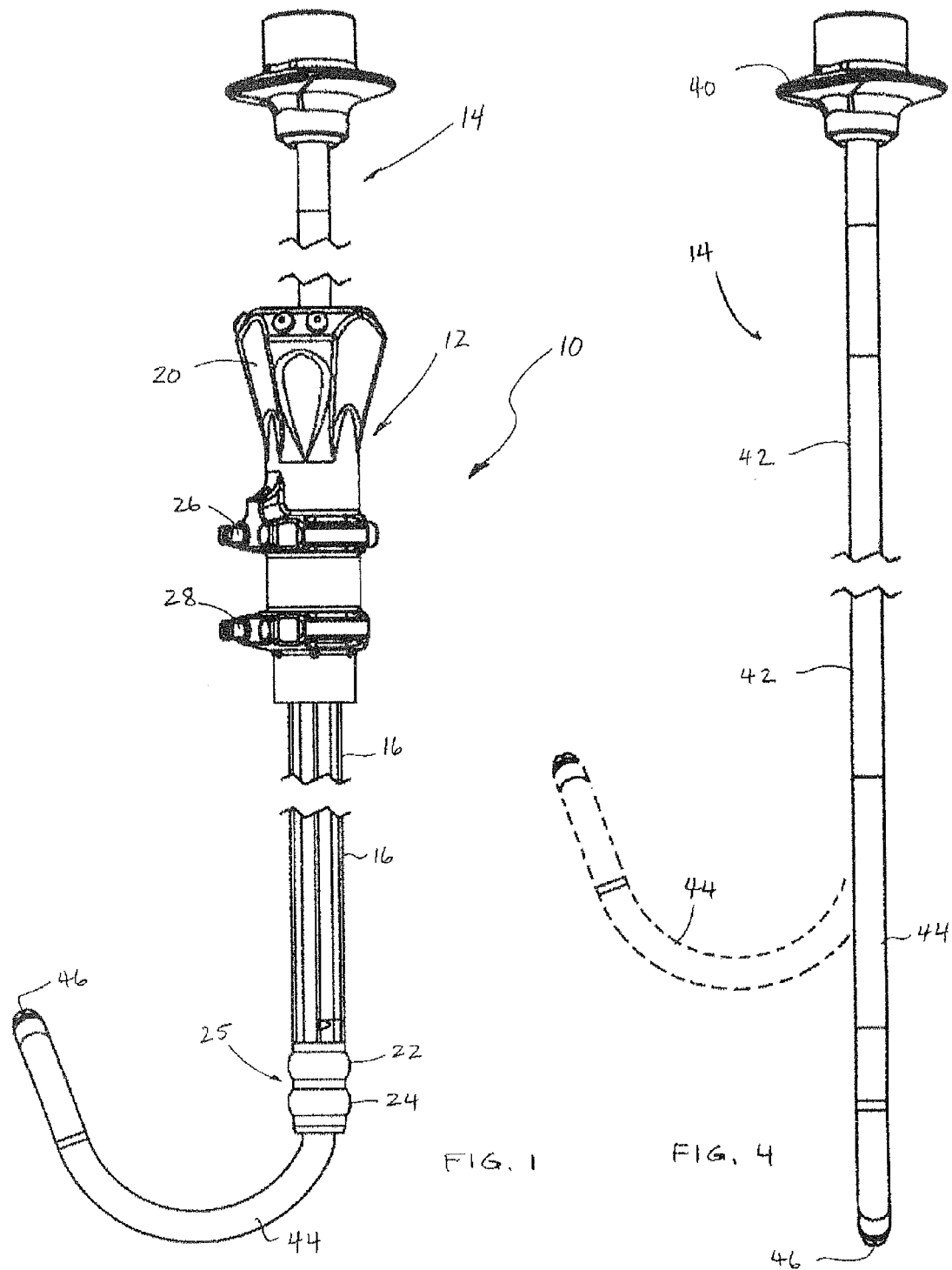

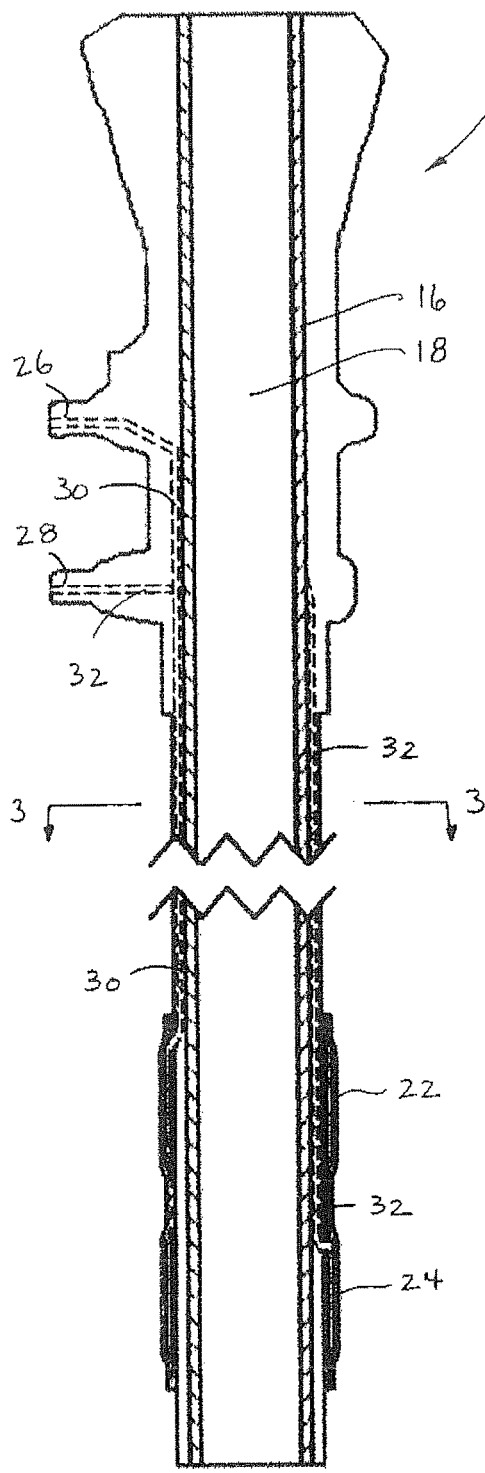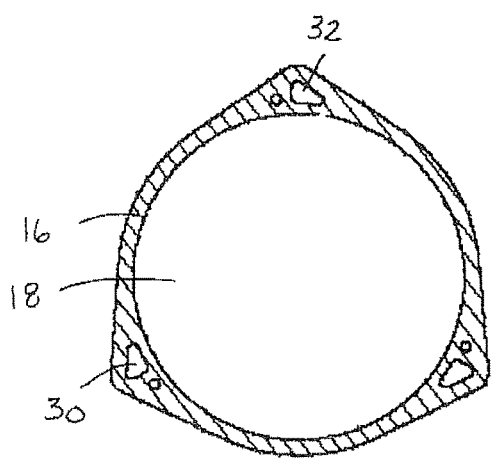
FIG. 3
FIG. 2

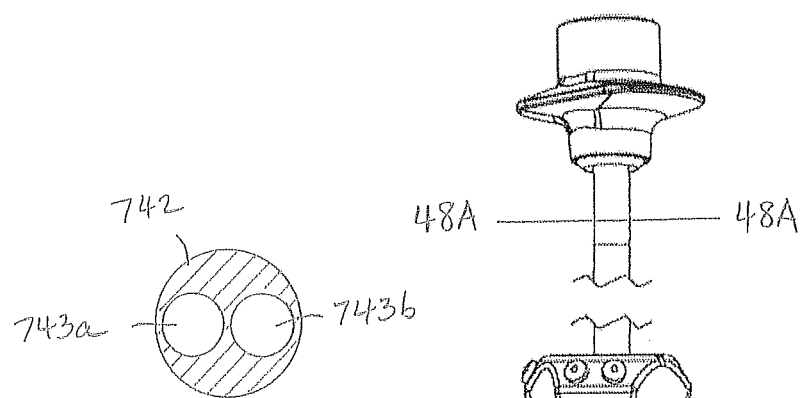
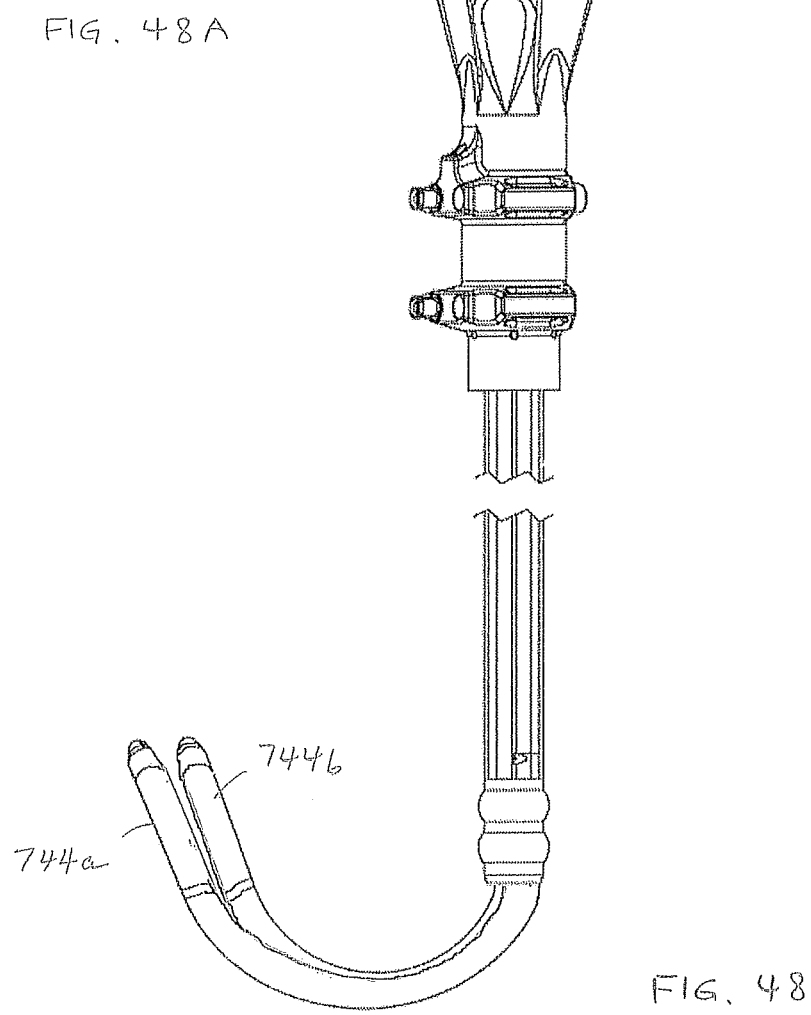
FIG. 48A
FIG. 48

ACCESS SYSTEMS AND METHODS OF INTRA-ABDOMINAL SURGERY

CROSS-REFERENCE TO RELATED APPLICATIONS

This application is a divisional of U.S. Ser. No. 12/121,409, filed May 15, 2008, now abandoned, which is hereby incorporated by reference herein in its entirety.

This application is related to U.S. Ser. No. 11/775,996, filed Jul. 11, 2007, and U.S. Ser. No. 12/030,244, filed Feb. 13, 2008, which are hereby incorporated by reference herein in their entireties.

BACKGROUND OF THE INVENTION

Field of the Invention

The present invention relates to access systems for accessing and providing access to the peritoneal cavity via a body cavity accessible through a natural orifice, and methods of performing intra-abdominal surgical procedures through such an access system using an endoscope.

State of the Art

Traditional gallbladder removals are either performed via laparoscopic or open surgery techniques Laparoscopic procedures utilize electrocautery electrodes to dissect the gallbladder. These electrodes remain dangerously hot and may cause damage to adjacent viscera. Moreover, the surgical approach requires a large wound or several holes through the abdominal wall.

The field of gastrointestinal endoscopy has for many years been limited to diagnostic and therapeutic techniques to observe, modify and remove tissues located in the digestive tract. Only recently have there been efforts to expand gastrointestinal endoscopic surgery to within the peritoneal cavity to remove large tissue masses such as the appendix and gallbladder. Generally, in these newer procedures, a natural orifice transluminal endoscopic surgery (NOTES) access system is used to gain access to the peritoneal cavity through the stomach or another natural orifice. However, there are still significant limitations to the techniques for visualizing, manipulating and removing masses of tissue on current NOTES systems. In particular, once the NOTES system is in place, an endoscope is used to navigate instrumentation to the subject tissue for removal. Endoscopes are limited in their maneuverability, generally having only a single axis along which they can be bent to direct instrumentation.

Further, the en bloc removal of large tissue masses, such as the gallbladder, presents numerous problems for current endoscopic tools and techniques. Currently, access to and removal of these types of tissue masses requires tissue separation and dissection that can be particularly difficult from an endoscopic approach. Also, after removal of tissues from the surgical site, current system require extremely skilled closure techniques. These closure techniques can prevent acceptance of such procedures from a large number of even skilled surgeons and also greatly increase the time for completing a procedure and the safety of the patient.

SUMMARY OF THE INVENTION

According to embodiments of the invention, an access system is provided for enabling and facilitating access to the peritoneal cavity from a body cavity accessible through a natural orifice, such as an intragastric approach or a transvaginal approach. The access system includes a proximal handle, an overtube coupled to the handle, and an endoscope port extending through handle and overtube sized for receiving an endoscope therethrough. The overtube includes a securing system that secures a distal portion of the overtube within a hole in an anatomical wall of a body cavity accessible through a natural orifice. In a preferred embodiment, the securing system includes proximal and distal inflatable cuffs provided on an external portion of the overtube. The cuffs are coupled to discrete injection ports extending from the handle through the overtube that permit individual pressurization to fixate the cuffs on opposite sides of the anatomical wall. The anatomical wall can be captured between the two cuffs to secure the access system to the anatomical wall and provide a seal between the space of the natural orifice accessible body cavity (e.g., intragastric space) and the peritoneal cavity. The overtube is also provided with a shaped distal portion or a controllably shapeable distal portion that aids in directing an endoscope inserted through the port to a particular location within the peritoneal cavity. The access system is optionally provided with means for insufflating/deflating the peritoneal space separately from the body cavity (e.g. intragastric space). In addition, the access system optionally includes a closure means for deploying and acting on fastening to effect closure of the hole made in the anatomical wall in which the access system is secured to seal the hole after the access system has been removed from the hole.

In one embodiment, the preshaped distal portion of the access system is a preshaped portion of a port separate from the overtube and extendable therethrough. The preshaped port is molded or otherwise formed with a biased shape to aid in directing an endoscope to a particular location within the peritoneal cavity. After the overtube is inserted into the patient, the preshaped port is inserted through the overtube, which initially counters the bias so that the biased distal portion of the port straightens as its passes through the overtube. Once the distal portion of the port exits the distal end of the overtube, the port assumes the shape of its preshape, thereby able to direct an endoscope or other instruments to a designated structure. The port can be rotated within the overtube to redirect the instruments. At the conclusion of the procedure, the port is withdrawn from the overtube and then the overtube is removed from the patient.

In another embodiment, the preshaped distal portion is configured from an integral tubular element that is cut to define segmental recesses or cut-outs along its length. One or more pull wires extend from the handle of the access system to the distal end. When the appropriate pull wire(s) is/are activated at the handle, the tubular element bends along the cutouts and can be maintained in such configuration to orient the endoscopic port toward the target tissue. If necessary to reconfigure the access port or at the conclusion of the procedure, the handle can be operated to release the tension on the wire(s) and straighten the distal portion to aid in withdrawing the access port from the patient.

The means to control insufflation/deflation includes a first port extending from the handle to a location intermediate the handle and the proximal cuff, and a second port extending from the handle to a location at or distal the distal cuff. The handle is also provided with a gas control system to inject or evacuate air through the respective first and second ports. In embodiments including means to control insufflation/deflation, the endoscopic port includes a seal sealing valve, preferably located within the handle. In this manner, once the cuffs have separated the natural orifice from the peritoneal space, the pressures in the peritoneal space and natural orifice accessible body cavity can be separately controlled, e.g., to reduce stomach pressure while maintaining peritoneal pressure to provide increase visibility at the surgical site.

The closure means facilitates rapidly closure of the hole in the anatomical wall. In one embodiment, the closure means includes a cinching system preferably incorporating T-tags. In such embodiment, the access port is operable to implant hollow needles in a spaced apart manner about the hole. The access port is then operable to insert T-tags having a trailing suture through the hollow needles. Then, means are integrated with the access port or an independent tool is operable therewith that cinches the suture of the T-tags together about the hole to effect closure at the appropriate point in the procedure.

The access system facilitates methods of getting through the anatomical wall. According to a first method, described with respect to an intragastric approach, an initial piercing is made from the exterior of the stomach to the interior of the stomach. According to a second method, also described with respect to an intragastric approach, an initial piercing is made from the interior of the stomach to the exterior of the stomach. Both methods include the dilatation of the stomach piercing using a balloon catheter. Once inside the peritoneal cavity and sufficiently oriented towards a surgical site a medical procedure can be conducted. By way of example, the gallbladder can be separated from the liver using tunneling and dissection balloons. Such methods are also useable in a transvaginal approach to a medical procedure.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation of a first embodiment of an access system according to the invention.

FIG. 2 is a broken section view of an overtube of the access system of FIG. 1.

FIG. 3 is a cross sectional view across line 3-3 in FIG. 2.

FIG. 4 is a broken side elevation view of a shaped port device of the access system of FIG. 1, shown in two different configurations.

FIG. 48 is broken side elevation view of a third embodiment of an access system according to the invention.

FIG. 48A is a cross-section across line 48A-48A in FIG. 48.

FIG. 55 illustrates the access system being used to deploy fasteners through the hollow needle and the stomach wall.

FIG. 57 illustrates the access system being used to cinch the fasteners together about a hole in the stomach wall to provide closure of the hole.

DETAILED DESCRIPTION OF THE PREFERRED EMBODIMENTS

Figure 5:
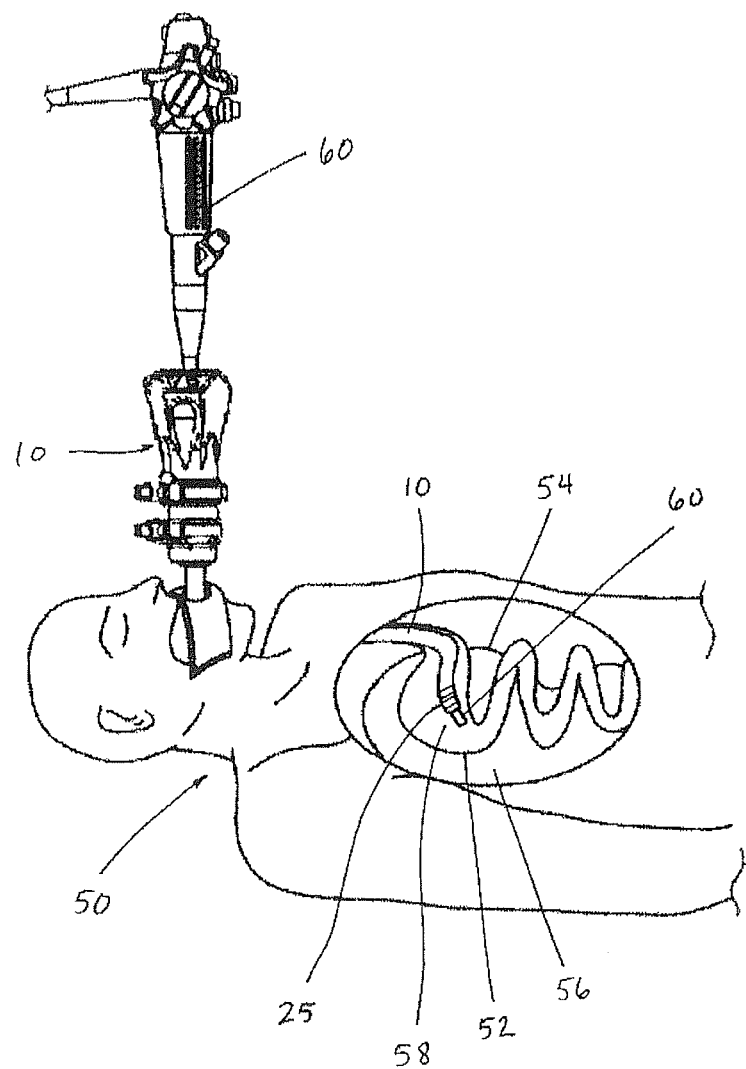
FIGS. 5 through 21 illustrate methods of securing the access system of FIG. 1 within the stomach wall to access the peritoneal cavity.

Turning now to FIGS. 1 through 3, a natural orifice transluminal endoscopic surgery (NOTES) access system 10 is provided for enabling and facilitating access to the peritoneal cavity through an anatomical wall, the anatomical wall separating the peritoneal cavity and a natural orifice accessible body cavity. While the invention is primarily described with respect to a through-the-esophagus transgastric approach for such surgery, where the body cavity is the stomach and the anatomical wall is the stomach wall, the systems and methods described herein are equally applicable to procedures performed transanally, wherein the body cavity is the colon and the anatomic wall is the colon wall, and transvaginally wherein the body cavity is the vagina and the anatomic wall is the vaginal wall.

The access system 10 includes an overtube 12 and a discrete preshaped port 14 insertable therethrough. The overtube 12 includes a first tubular member 16, a circular lumen 18 defined through the center of the first tubular member, and a handle 20 provided at the proximal end of the first tubular member 16. The overtube 12 has length in the range of 10 to 50 inches with a preferred range of 25 to 35 inches; a lumen diameter in the range of about 8 to 18 mm; and an outer diameter in the range of about 10 to 25 mm. The overtube 12 includes a gastric wall securing system that secures a distal portion of the overtube within a hole in the gastric wall. In a preferred embodiment, the gastric wall securing system includes proximal and distal inflatable cuffs 22, 24 provided on an external portion of the distal end 25 of the first tubular member 16. The cuffs 22, 24 are in communication with respective injection ports 26, 28 at the handle 20 through air channels 30, 32 to permit individual pressurization with a fluid, e.g., air, to fixate the cuffs on opposite sides of the gastric wall. This secures the overtube 12 to the gastric wall and provides a seal between the intragastric space and the peritoneal cavity, as described in more detail below.

The first tubular member 16 is sufficiently longitudinally flexible to assume the contour required for insertion through a patient's esophagus and into the stomach. Notwithstanding the longitudinally flexibility, the first tubular member preferably has sufficient lateral strength and stability to maintain the cross-sectional shape of the lumen along its length. Such strength may be provided by a metal or a polymeric coil or braid reinforcement along its length.

Referring to FIGS. 1, 2 and 4, the preshaped port 14 has a proximal instrument receiving end 40 and a second tubular member 42. The port 14 has length in the range of 20 to 60 inches, with a preferred range of 30 to 45 inches; a lumen diameter in the range of about 5 to 16 mm; and an outer diameter in the range of about 8 to 18 mm. The port body length is sufficient to extend from a patient's mouth to a patient's stomach or from any other natural orifice to a body cavity accessible therefrom. The receiving end 40 is sized to prevent passage through the lumen 18 of the overtube 12 and functions as a stop against the handle 20 of the overtube 12. The second tubular member 42 has a distal portion 44 preshaped so that it is biased to bend in a predetermined direction and preferably by a predetermined amount; i.e., the preshape is a portion biased to curve at a distal portion of the second tubular member 42 (as shown in broken lines in FIG. 4). The second tubular member 42 can be molded or extruded, and heat treated, provided with a metal or polymeric shape providing/effecting element, or otherwise formed with such biased shape. The preshape bias is readily overcome such that when the distal portion 44 is inserted through the lumen 18 of the first tubular member 16 of the overtube 12, the preshaped distal portion 44 straightens or otherwise conforms to the longitudinal shape of the first tubular member 16 of the overtube. However, once the preshaped distal portion 44 extends from the distal end of the overtube 16, the preshaped distal portion 44 of the port 14 conforms to its bias, thereby able to direct an endoscope or other instrument(s) extending within and through its lumen 46 toward a designated anatomical structure. The port 14 can be also rotated within the overtube 12 to further direct or redirect the endoscope and/or instrument(s) toward anatomical structures. The port 14 can be withdrawn together with or separately from the overtube 12 as the access system is removed from the patient.

Turning now to FIG. 5, a method of intra-abdominal surgery on a patient 50 using the access system 10 is now described. The access system 10 facilitates methods of accessing tissue 54 in the peritoneal cavity 56 through the stomach wall 52. According to a first method, described below, an initial piercing is made from the exterior of the stomach 58 to the interior of the stomach. According to a second method, also described below, an initial piercing is made from the interior of the stomach to the exterior of the stomach. Both methods include the dilatation of the stomach piercing using a balloon catheter to create a hole in stomach wall 52 of sufficient dimension to receive the distal end of the access system. The distal end of the access system is then anchored within the hole with cuffs 22, 24 (FIG. 1) at the distal end 25 of the access system. Once a passageway is provided through the access system 10 to the peritoneal cavity 56, the access system can be used to orient an endoscope 60 toward a tissue 54 in the peritoneal cavity 56, e.g., using the preshaped port, as described in more detail below. Then, by way of example, the tissue, such as the gallbladder, can be separated from other tissue, such as the liver, using tunneling and dissection balloons or other techniques.

Figure 6:
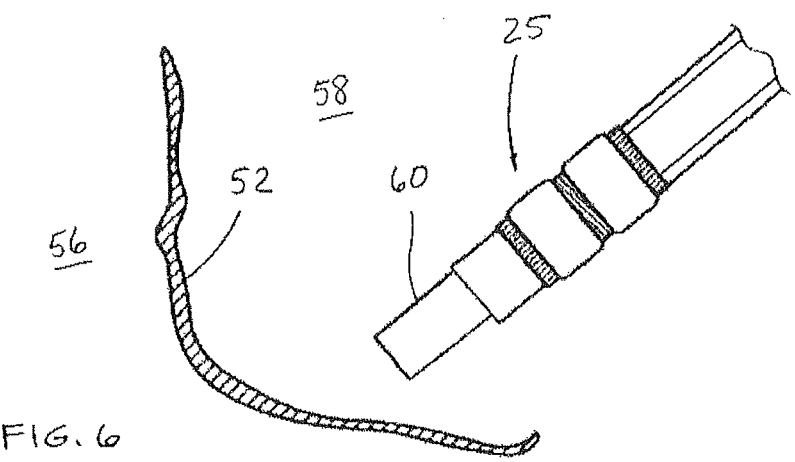

More particularly, turning now to FIGS. 5 and 6, with the port 14 (FIGS. 1 and 4) removed from the access system 10, a steerable endoscope 60 is inserted through the lumen of the overtube 12. The overtube 12 and endoscope 60 are inserted together into the stomach 58 of the patient 50, with the endoscope 60 steering the assembly through the natural orifices, esophageal sphincter, and into the stomach. The distal end 25 of the overtube 12 with the endoscope is maneuvered adjacent the stomach wall 52.

Figure 7:
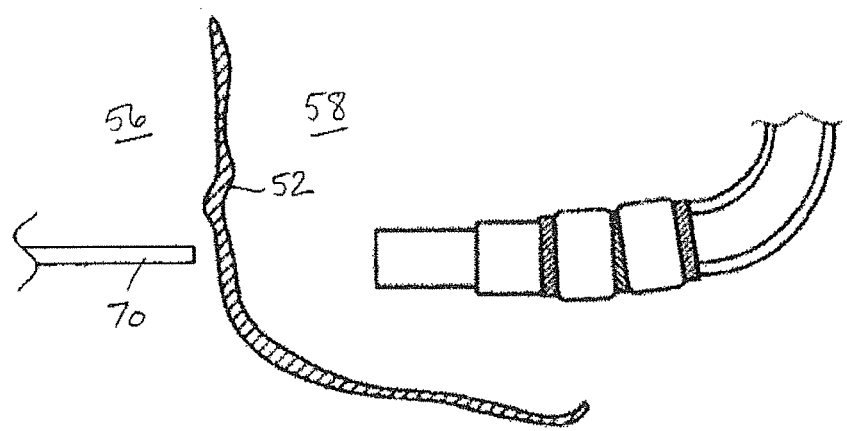
Figure 8:
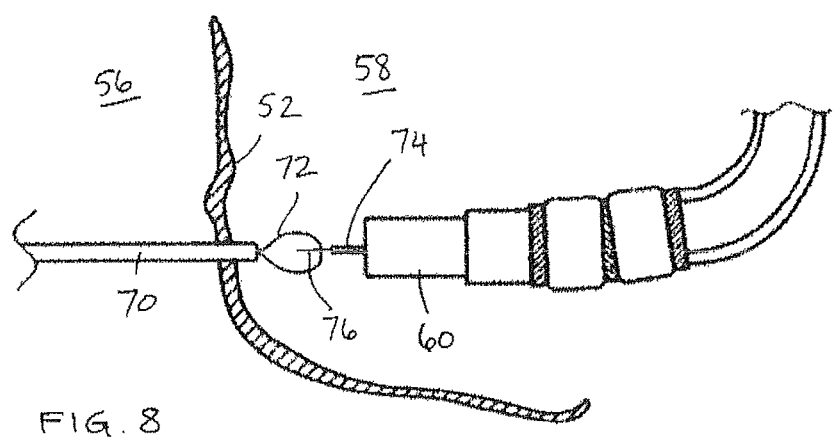

Referring to FIGS. 7 and 8, in accord with one embodiment of the method, a piercing catheter (or other preferably tubular piercing/cutting instrument) 70 is inserted into the patient's peritoneal cavity 56 from outside the stomach wall 52. The piercing catheter 70 can be provided into the peritoneal cavity 56 by insertion through the abdominal wall, by introduction up the colon via an endoscope and then piercing through the colon into the peritoneal cavity 56, or by introduction through the vagina. The piercing catheter 70 is pierced through the stomach wall 52 and introduced into the stomach 58.

Referring to FIG. 8, a snare device 72 is introduced through the piercing catheter 70 and into the stomach 58. A balloon catheter 74 fixed along a guidewire 76 is introduced into the stomach 58 through the endoscope 60. The guidewire 76 is preferably integrated with the balloon catheter 74.

Figure 9:
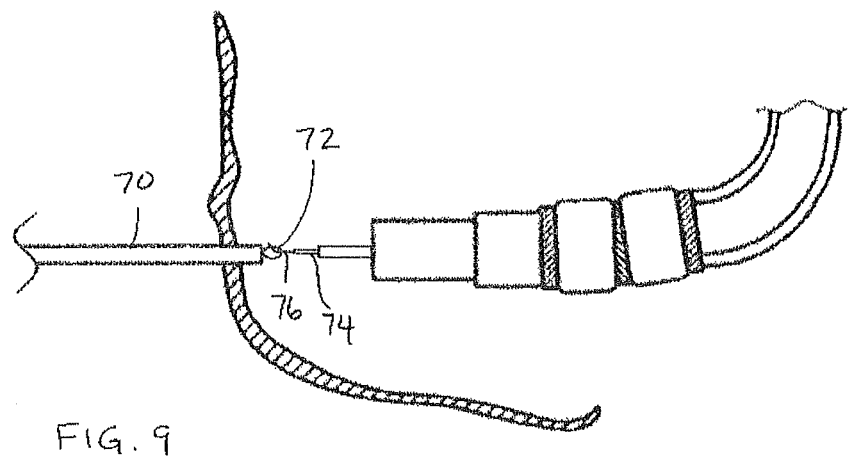
Figure 10:
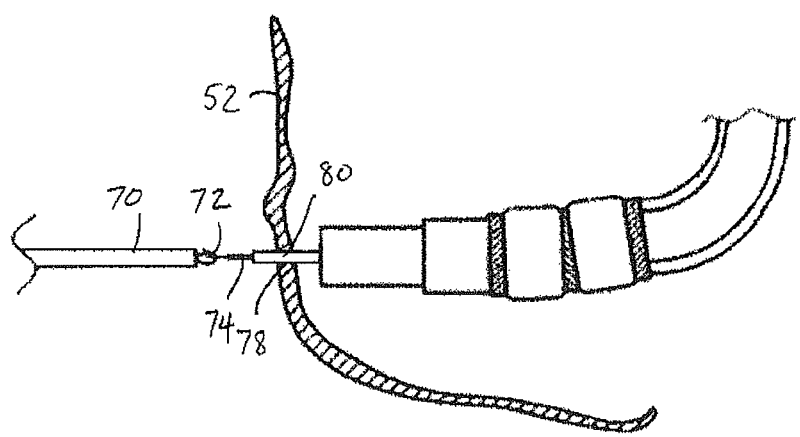
Figure 11:
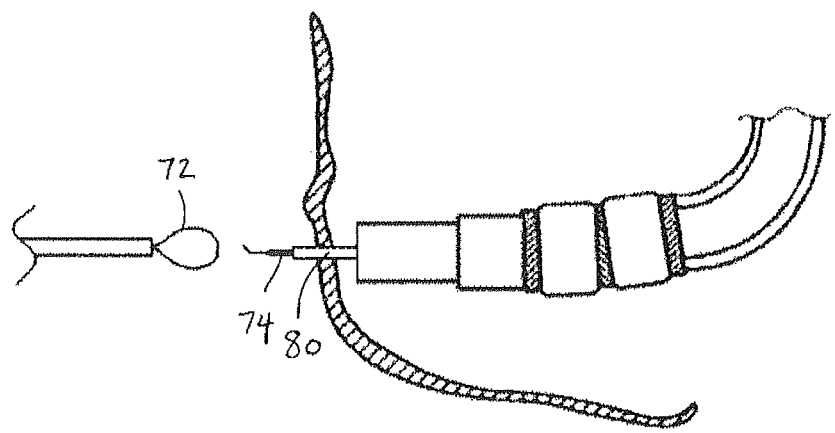

Referring to FIGS. 9 and 10, the snare device 72 and cutting instrument 70 are operated to grasp the guidewire 76 and/or balloon catheter 74, and pull the balloon catheter 74 through the piercing 78 in the stomach wall 52. Once the balloon 80 on the balloon catheter 74 is positioned within the piercing 78, the snare device 72 releases the guidewire 76 and/or balloon catheter 74 so as to decouple the snare device 72 from the balloon catheter 74, as shown in FIG. 11.

Figure 12:
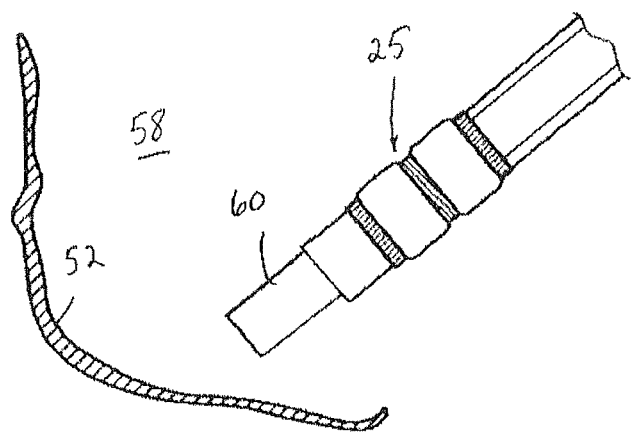
Figure 13:
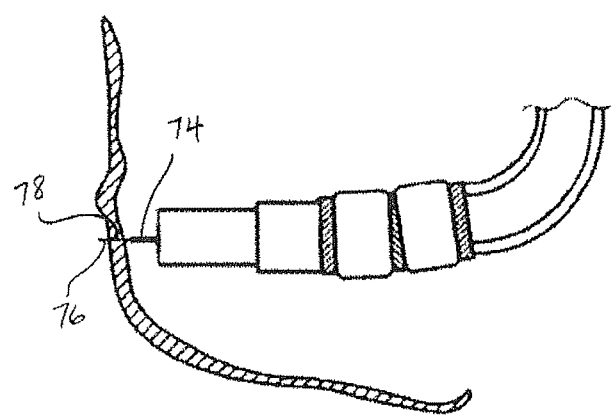
Figure 14:
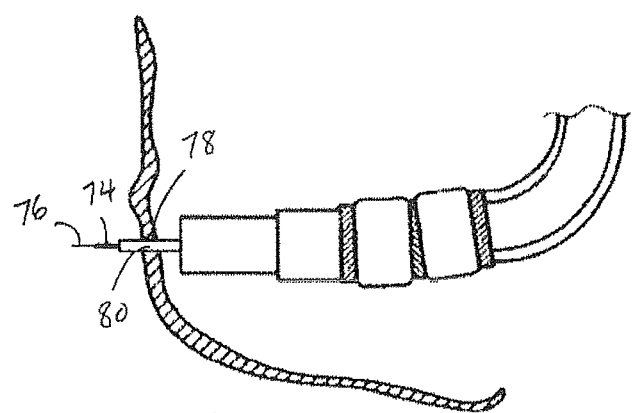

Referring to FIGS. 12 through 14, in accord with an alternate embodiment of positioning a balloon catheter within a piercing in the stomach wall, once the distal end 25 of the overtube and endoscope 60 are positioned within the stomach 58 adjacent the stomach wall 52, a cutting instrument (not shown) is advanced through the endoscope (or a port provided within the overtube) to define a piercing 78 in the stomach wall 52 from the interior of the stomach. The guidewire 76 and balloon catheter 74 are then advanced through the piercing to position the balloon 80 within the piercing 78.

Figure 15:
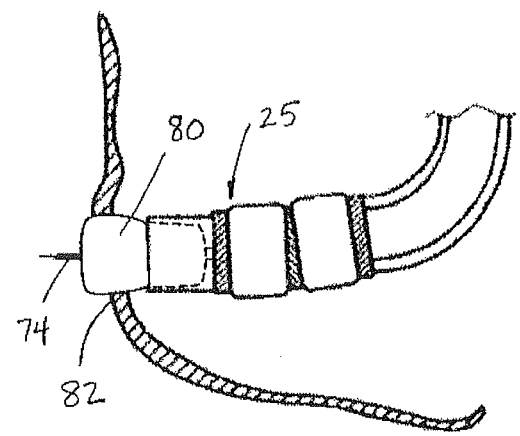
Figure 16:
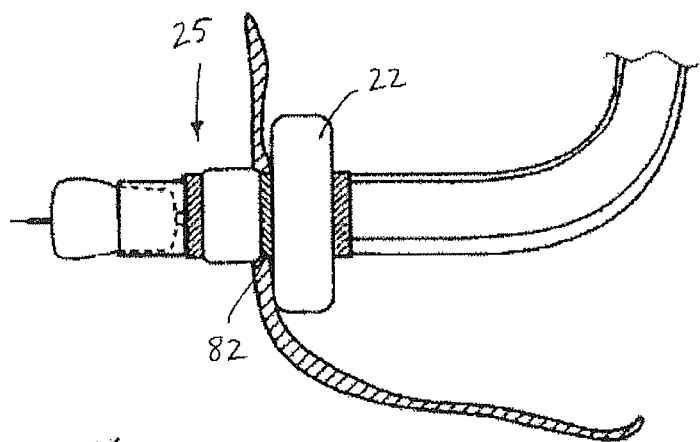
Figure 17:
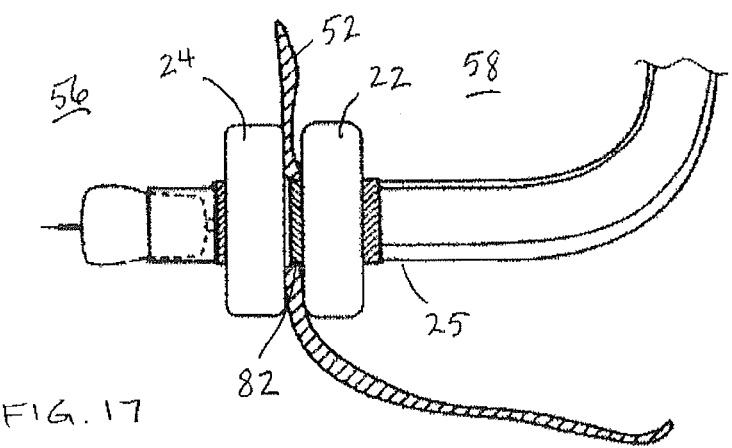

Then, referring to FIGS. 15 through 17, regardless of the method used to position the balloon 80 within the piercing 78, the balloon 80 is expanded upon activation from outside the patient by pressurizing a fluid through the balloon catheter 74. The balloon 80 can be located partially inside the distal end 25 of the overtube (as shown) or completely external the distal end of the overtube. As the balloon 80 is expanded, the piercing 78 (FIG. 14) is dilated to create a hole 82 of sufficient size to receive the distal end 25 of the overtube. The proximal cuff 22 is expanded, and the distal end 25 of the overtube is inserted through the hole 82 up to cuff 22. Then the distal cuff 24 is expanded to secure the distal end 25 of the overtube to the stomach wall 52 between the proximal and distal cuffs 22, 24 and to thereby provide a seal between the intragastric space (at the stomach 58) and the peritoneal cavity 56.

Figure 18:
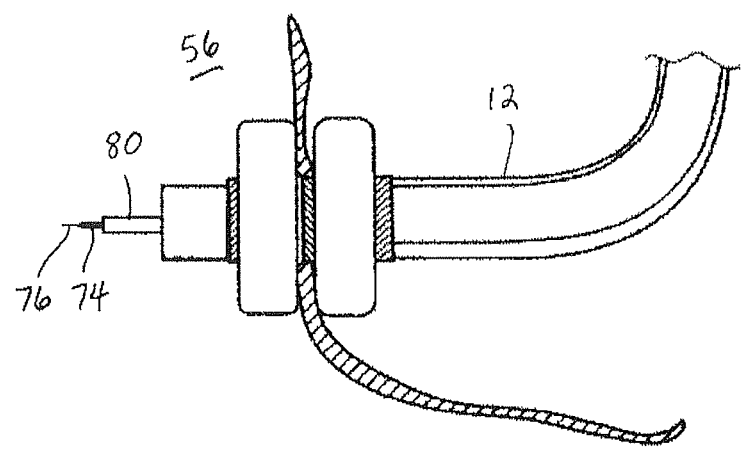

Referring to FIG. 18, the balloon 80 is deflated, and the balloon catheter 74 and guide 76 are withdrawn from the overtube 12. The endoscope 60 (FIG. 12) can then be used within the peritoneal cavity 56 along with other instruments advanced within the overtube.

Figure 19:
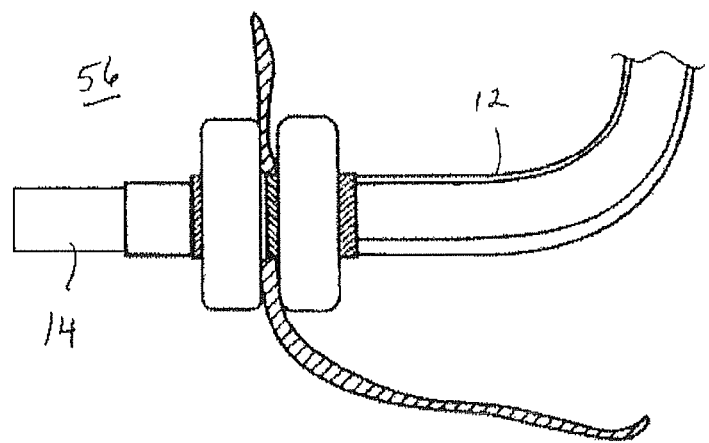
Figure 20:
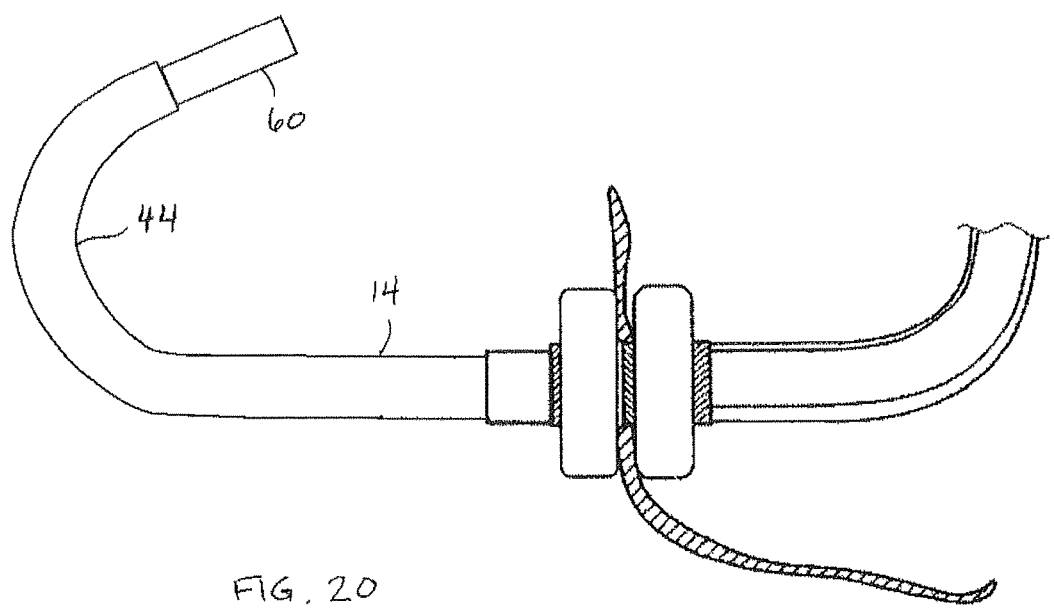
Figure 21:
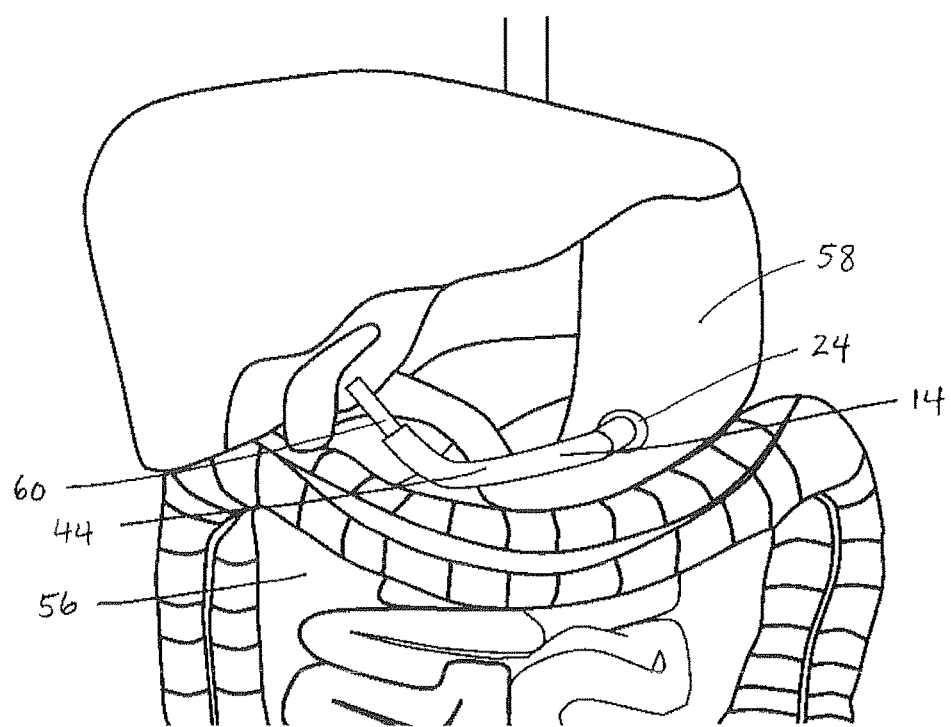

However, referring to FIGS. 19 through 21, in accord with a preferred aspect of the method, the endoscope is also withdrawn from the overtube 12 and the preshaped port 14 is advanced through the overtube 12 into the peritoneal cavity 56. As the preshaped port 14 is advanced to an extent allowing the preshaped distal portion 44 to bend in accord with it preshaped bias, the port 14 will provide a predefined (although rotationally orientable) pathway for re-introduction of the endoscope 60 into the peritoneal cavity 56. The endoscope 60 is then reintroduced through the port 14.

It is appreciated that various surgical procedures can be performed once the endoscope and other instruments are located in the peritoneal cavity. For example, the access system 10 can be used to perform a cholecystectomy, or dissection of the gallbladder from the liver. In accord with a preferred method of performing a cholecystectomy, tunneling and dissecting instruments, as disclosed in previously incorporated U.S. Ser. No. 11/775,996, are preferably used in conjunction with the access system 10. While detailed descriptions of suitable instruments are described in the aforementioned application, it is helpful to generally describe the tunneling and dissection instruments here for a point of reference.

Figure 22:
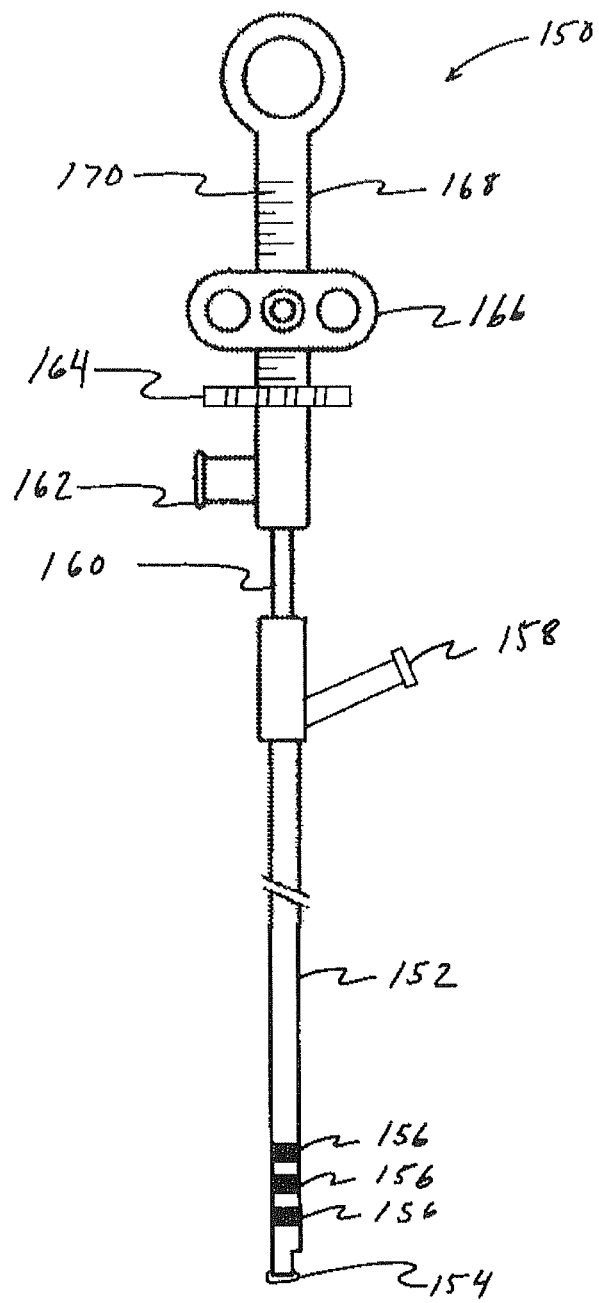
FIG. 22 is broken side elevation view of a balloon tunneling device for use with methods of the invention.
Figure 23:
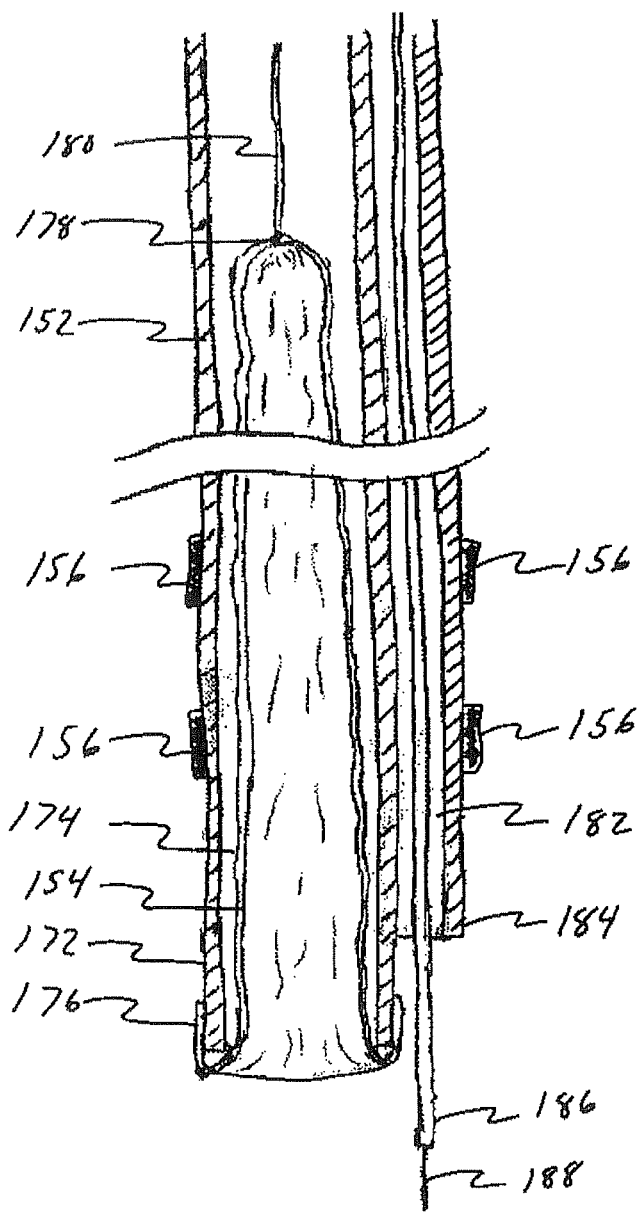
FIG. 23 is an enlarged broken longitudinal section view of the distal end of the balloon tunneling device of FIG. 22.

Referring to FIG. 22, a tunneling instrument 150 includes a catheter 152 having proximal and distal ends and a balloon member 154 located adjacent the distal end. Positioned on the exterior of catheter 152 adjacent the distal end is a series of markers 156. These markers may be visible under direct visualization of the endoscope and may be additionally visible under fluoroscopy. Adjacent the proximal end of catheter 152 is an auxiliary device port 158. The proximal end of catheter 152 is attached to connector tubing 160 to access inflation port 162. Valve assembly 164 provides a seal for fluid introduced into inflation port 162. Tether slide 166 is slidably positioned on handle body 168. Handle body 168 includes distance markers 170 to gauge the movement of tether slide 166. A cross sectioned view of the distal end of tunneling instrument 150 is shown in more detail in FIG. 23. Catheter 152 has a distal end 172 and a first lumen 174. Located within first lumen 174 is balloon member 154. The balloon member 154 is preferably non-compliant of the type generally known in the art, however, balloon member 154 may be of the compliant or semi-compliant type. The balloon member 154 may be formed from biocompatible polymer types such as olefins, elastomers, thermoplastic elastomers, vinyls, polyamides, polyimides, polyesters, fluropolymers, copolymers and blends of any of the aforementioned. The proximal end 176 of balloon member 154 is attached to the distal end 172 of catheter 152. The distal end 178 of balloon member 154 is positioned within the first lumen 174 in an everted configuration. A tether member 180 is connected to the distal end 178 of balloon member 154. Tether member 180 is flexible and preferably takes the form of a filament, as shown, however tether member 180 may take the form of a tube. The proximal end of tether member 180 is connected to tether slide 166 through valve assembly 164. Tether member 180 aids in initially positioning balloon member 154 within the first lumen 174 of catheter 152. Catheter 152 has a second lumen 182 that extends from auxiliary device port 158 to distal end 184. Distal end 184 is located proximal to distal end 172 of catheter 152. Slidably disposed within second lumen 182 is a needle knife 186 that has a knife tip 188. Needle knife 186 is preferably of the endoscopic electrosurgical type however any form of incision device that may be operated to form an incision in tissue such as mechanical cutters, water jets or lasers may be suitable.

Figure 24:
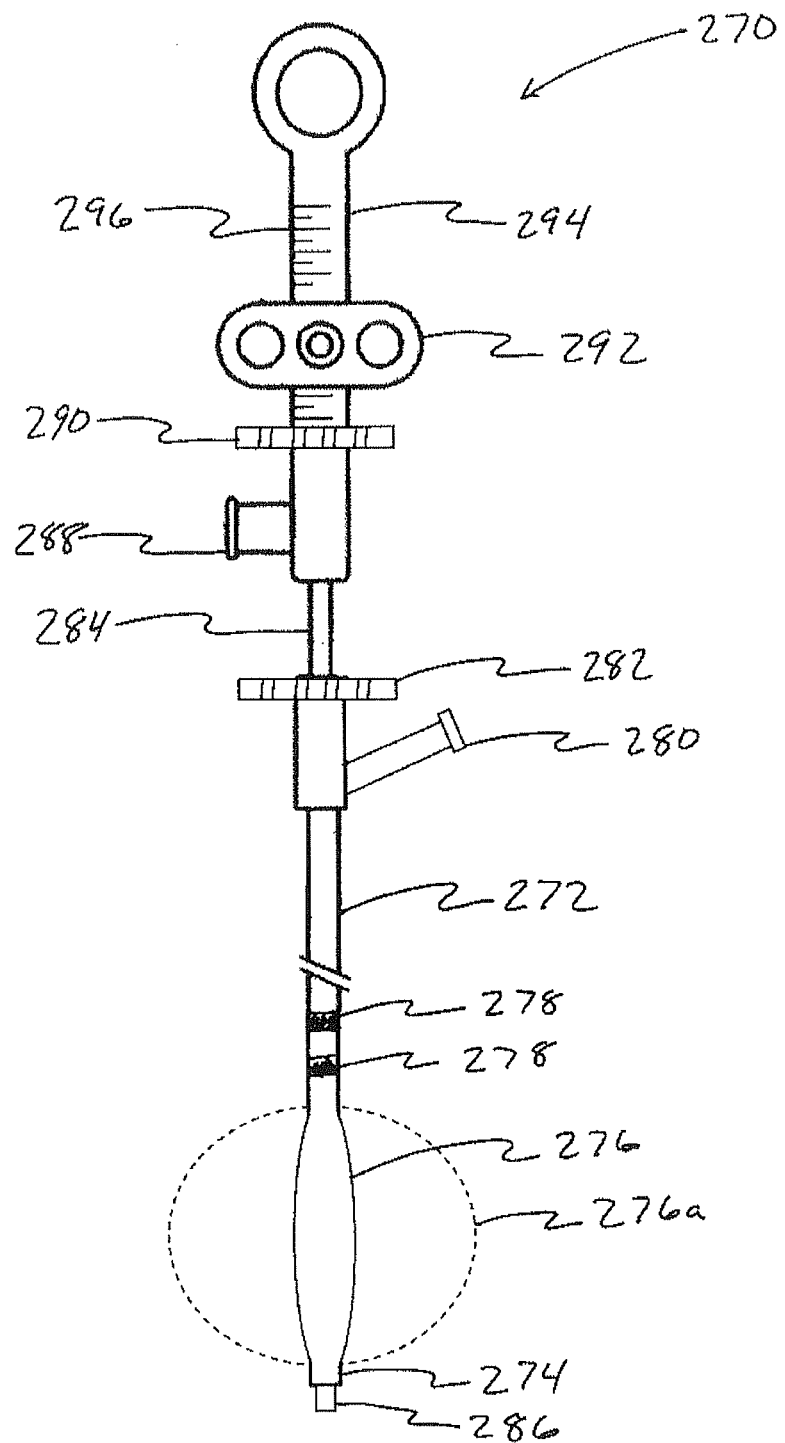
FIG. 24 is broken side elevation view of a balloon dissection device for use with methods of the invention, with the balloon shown in collapsed and expanded states.

Further, referring to FIG. 24, a dissecting instrument 270 is provided and includes a dissection catheter 272 having a distal end 274 and a dissection balloon 276 having a large diameter expanded dissection balloon configuration 276a that operates to separates adjacent tissues. The dissection balloon 276 can be non-compliant of the type generally known in the art or dissection balloon 276 may be of the compliant or semi-compliant type. The dissection balloon 276 may be formed from biocompatible polymer types such as olefins, elastomers, thermoplastic elastomers, vinyls, polyamides, polyimides, polyesters, fluropolymers, copolymers and blends of any of the aforementioned. The dissection catheter 272 has insertion markers 278 positioned along its shaft. The proximal end of dissection catheter 272 includes both an inflation port 280 that is in fluid communication with dissection balloon 276, and a valve assembly 282.

Figure 25:
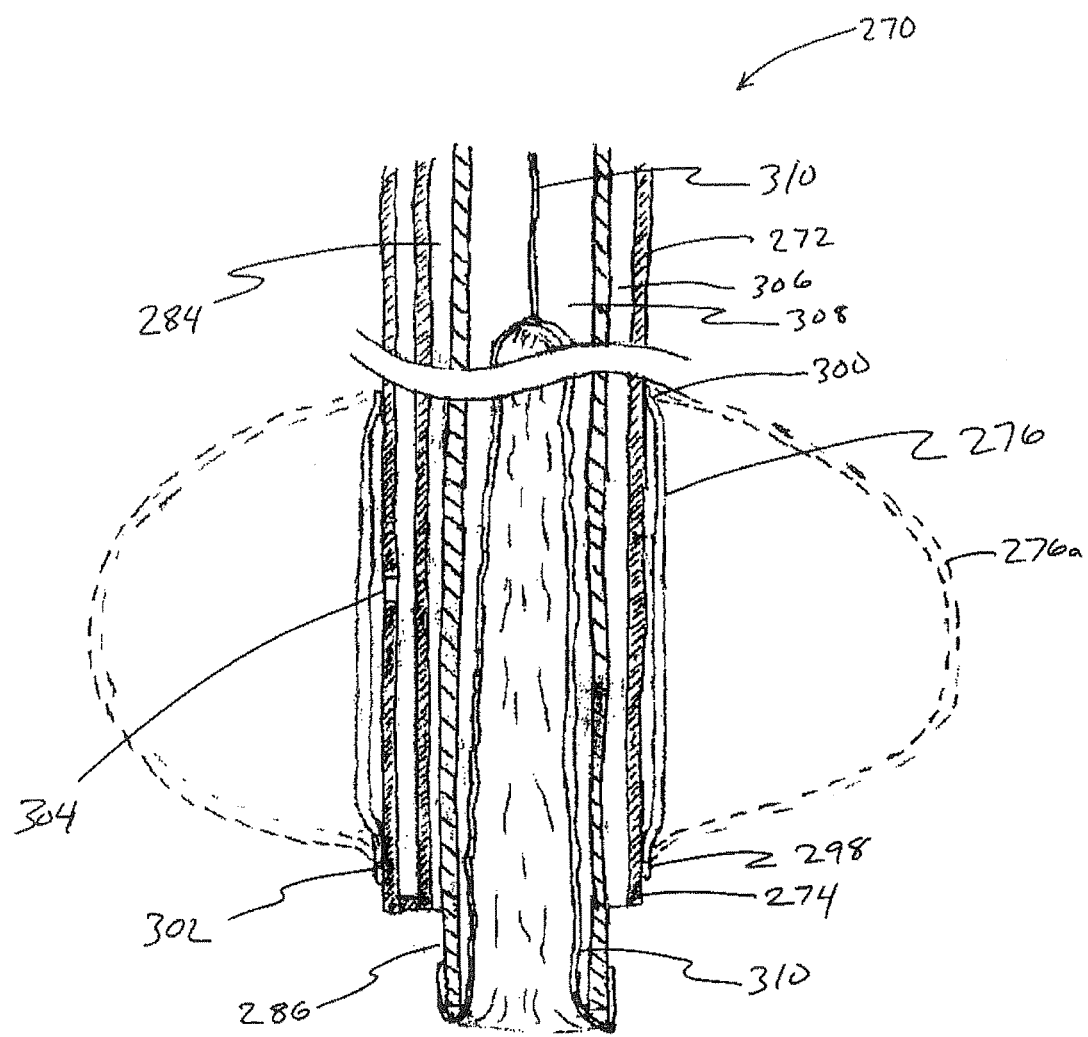
FIG. 25 is an enlarged broken longitudinal section view of the distal end of the balloon dissection device of FIG. 24.
Figure 26:
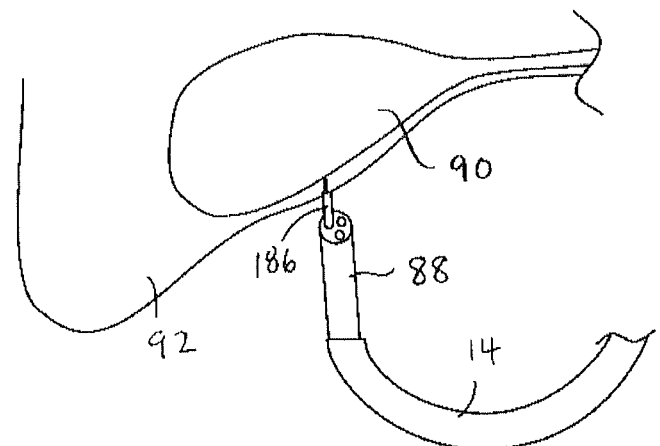
FIGS. 26 through 35 illustrate a method of performing an intra-abdominal surgery through the access system secured within the stomach wall.

In an embodiment seen from FIGS. 24 and 25, the dissecting instrument 270 is provided with tunneling capability to operate as a tunneling dissecting instrument. A tunneling catheter 284 is slidably disposed through valve assembly 282 and extends within a lumen of the dissection catheter 272. The tunneling catheter distal end 286 may extend beyond the dissection catheter distal end 274. Tunneling catheter 284 includes an inflation port 288 and valve assembly 290. A tether slide member 292 is slidably disposed on handle body 294 with distance markers 296. FIG. 26, illustrates a detailed cross section of the distal portion of the tunneling dissecting instrument 270. The distal end 298 and proximal end 300 of dissection balloon 276 are connected to the exterior of dissection catheter 272. An inflation device connects to inflation port 280 to inflate dissection balloon 276. Tunneling catheter 284 is slidably disposed within the lumen 306 of dissection catheter 272. Positioned within the lumen 308 of tunneling catheter 284 there is an everted expandable tunneling balloon 310. The tunneling balloon 310 is preferably non-compliant of the type generally known in the art, however, tunneling balloon 310 may be of the compliant or semi-compliant type. The tunneling balloon 310 may be formed from biocompatible polymer types such as olefins, elastomers, thermoplastic elastomers, vinyls, polyamides, polyimides, polyesters, fluropolymers, copolymers and blends of any of the aforementioned. The distal end of tunneling balloon 310 is connected to a tether member 312 which has a proximal end that is connected to tether slide 292.

The operation of the tunneling dissecting instrument 270 to form a tunnel and large dissected area is similar to the operation of the separate instruments. The tunneling catheter 284 is pressurized with fluid to linearly expand tunneling balloon 310. The temperature of the tunneling balloon 310 may be modified, e.g., cooled, via the fluid introduced therein to reduce bleeding. Once a tunnel has been formed, tunneling balloon 310 may be deflated and dissection catheter 272 may be advanced through the opening into the tunnel. The markers 278 may be used to determine the depth in which the dissection catheter 272 has been advanced into the tunnel. Once the dissection catheter 272 has been properly positioned within the tunnel it may be operated. By applying pressurized fluid to inflation port 280, dissection balloon 276 is dilated to an expanded dissection balloon 276a configuration. During the expansion, a dissected area is created. The temperature of the dissection balloon 276 may be modified, e.g., cooled, via the fluid used therein to reduce bleeding.

Other embodiments of tunneling and dissecting instruments disclosed in U.S. Ser. No. 11/775,996 can also be used. Now with reference to such tunneling and dissecting instruments, an exemplar embodiment of a cholecystectomy procedure according to the invention is now described. First, access is provided to the peritoneal cavity using the access system, as described above.

Figure 27:
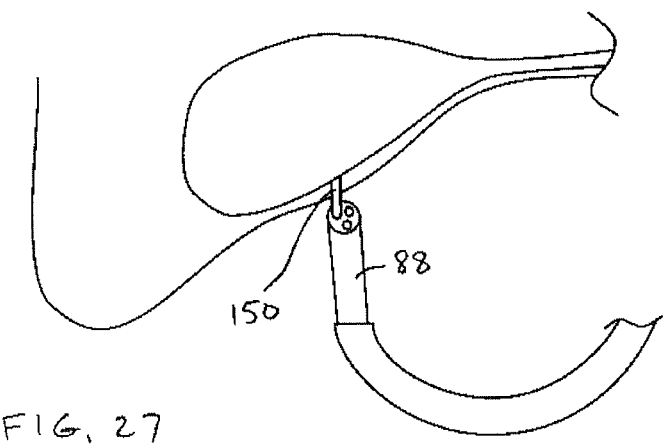
Figure 28:
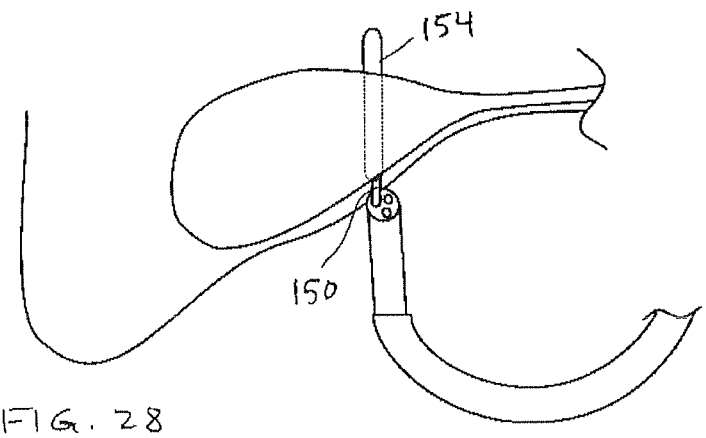
Figure 29:
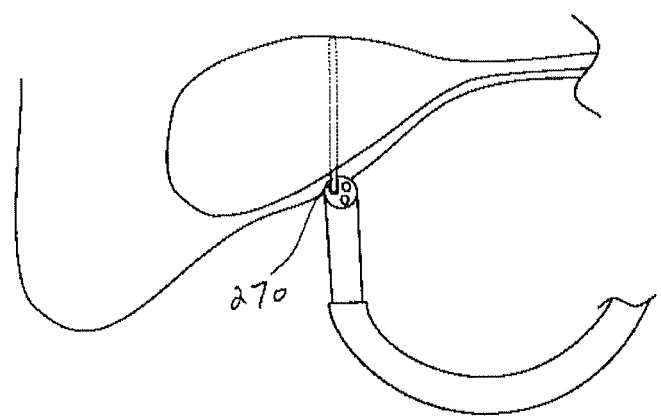
Figure 30:
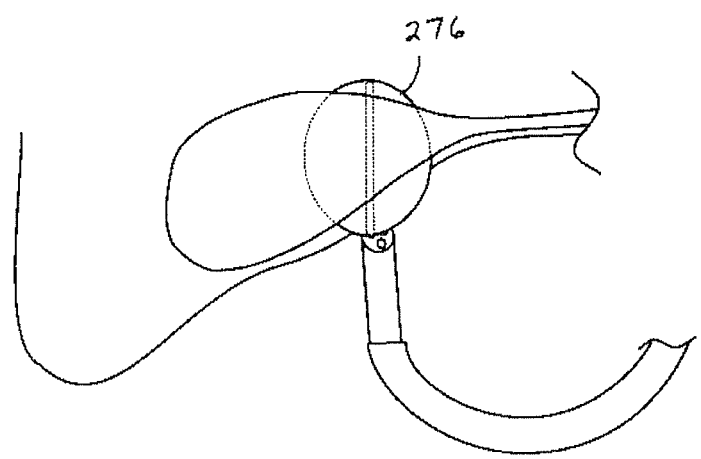
Figure 31:
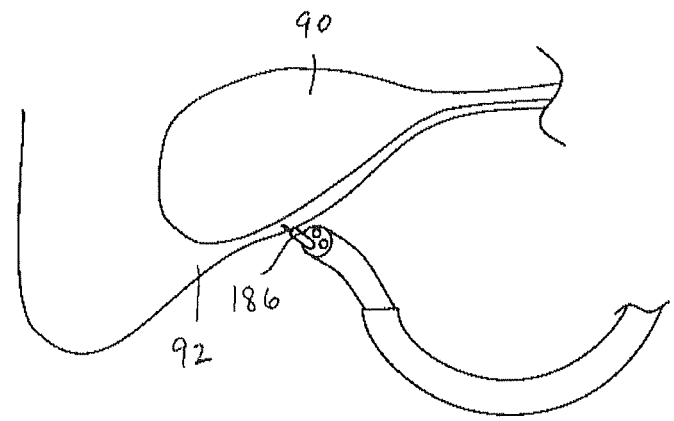
Figure 32:
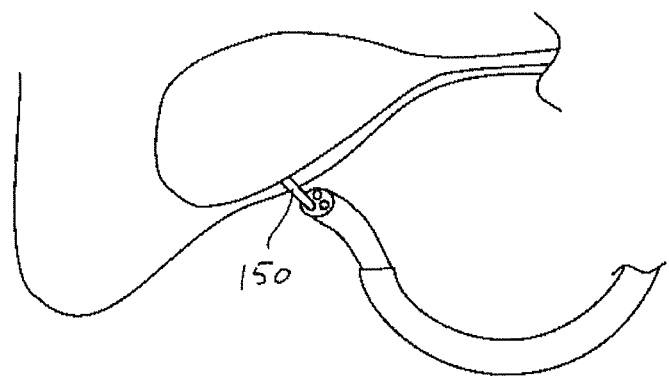
Figure 33:
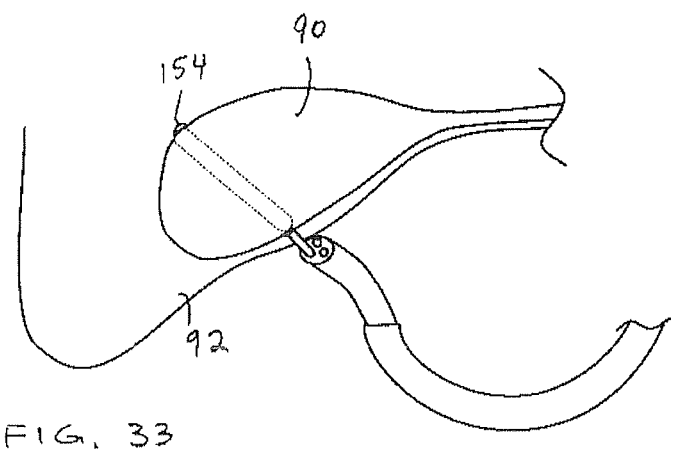
Figure 34:
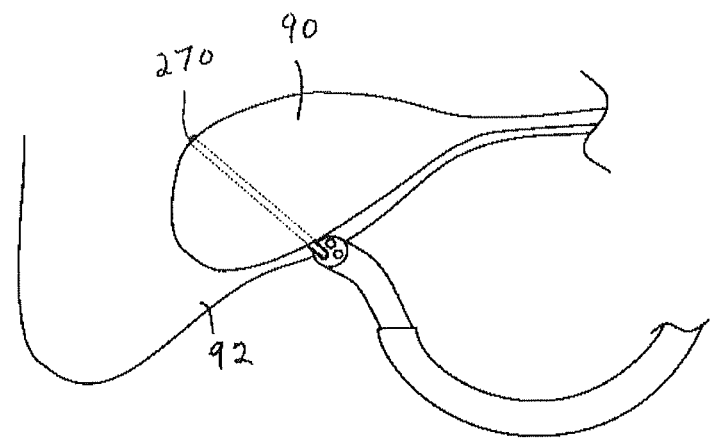
Figure 35:
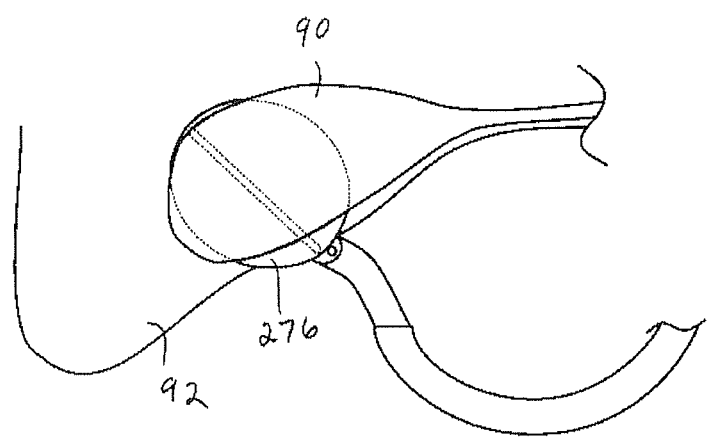

Then, referring to FIG. 26, a preferably multilumen device 88 is inserted through the shaped port 14 to a location such that the axis of a lumen of the device is directed between the gallbladder 90 and the liver 92. Multilumen device 88 preferably integrates an endoscope or includes a lumen for receiving an endoscope. A needle knife 186 is advanced through the lumen of the device 88 to define a small hole between the gallbladder 90 and liver 92. A tunneling instrument 150 is advanced into the hole in the tissue preferably through another lumen in the multilumen device 88 (FIG. 27). The needle knife 186 and tunneling instrument 150 may be integrated. The tunneling instrument 150 is operated to advance an elongate balloon member 154 to define an elongate tunnel in the tissue between the gallbladder and the liver (FIG. 28). If the tunneling instrument 150 is a separate instrument from the dissecting instrument, it is removed from the tunnel so that the dissecting instrument 270 can then be (and is) advanced into through another lumen of the multilumen device and into the tunnel (FIG. 29). The dissecting instrument 270 is then operated to expand the dissection balloon 276 within the tunnel to separate the tissues surrounding the balloon (FIG. 30).

Referring to FIGS. 31 through 35, the process is then repeated with the needle knife 186, tunneling instrument 150, and dissecting instrument 270 in different locations to substantially fully separate the gallbladder 90 from the liver 92. If necessary, an electrocautery knife, may be used to separate any remaining connection tissue. The multilumen device 88 permits multiple instrument use without requiring the physician to repeatedly change out the instruments. Of course, two or more of the instruments may be integrated into a single assembly. Further, the use of balloons to dissect the gallbladder (rather than electrocautery) is substantially safer and does not pose a threat to surrounding viscera.

The gallbladder may be completely resected by utilizing additional surgical instruments such ligators, electrocautery knives, and scissors for sealing off and separation of the cystic duct. The resected gallbladder may be placed in an endoscopically delivered specimen retrieval bag using tissue graspers. Once the gallbladder is secured in the retrieval bag, the bag may be withdrawn through the port lumen with the endoscope. Alternatively, if the specimen is too large for removal through the port, the specimen may be positioned adjacent the port distal end and withdrawn along with the port from the body.

Any instruments 150, 270, 184 remaining within the patient, the multilumen device 88, and the pre-shaped port 14 are removed from the overtube 12. Then the distal cuff 24 is deflated, permitting retraction of the overtube into the stomach. The proximal cuff 22 is also deflated. Appropriate instrumentation or means are also used to close the hole in the stomach wall. For example, clips, staples, sutures, other closures, ligatures and ligating bands, etc., can be used. Also, closure means integrated with the access system, as discussed below, can be integrated into any of the access systems described herein. Further, the instruments described can be used to perform dissections of other organs adhered to the abdominal wall or dissections of other tissues from organs. For example, the appendix can be removed by a similar procedure.

Figures 36, 36A:
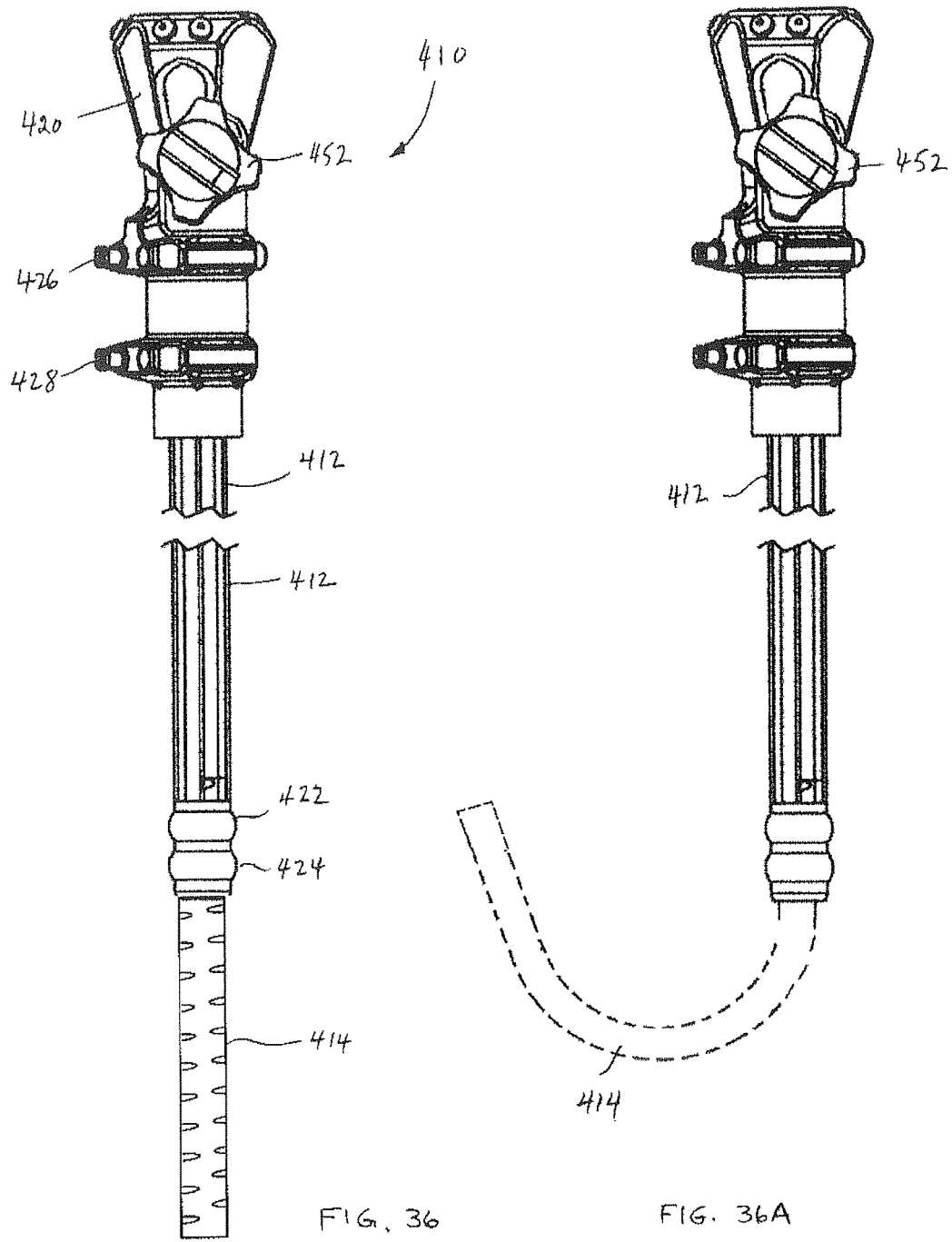
FIG. 36 is a broken side elevation of a second embodiment of an access system according to the invention.
FIG. 36A is a broken side elevation of the access system of FIG. 36, showing bending of the port into a pre-shape.
Figure 37:
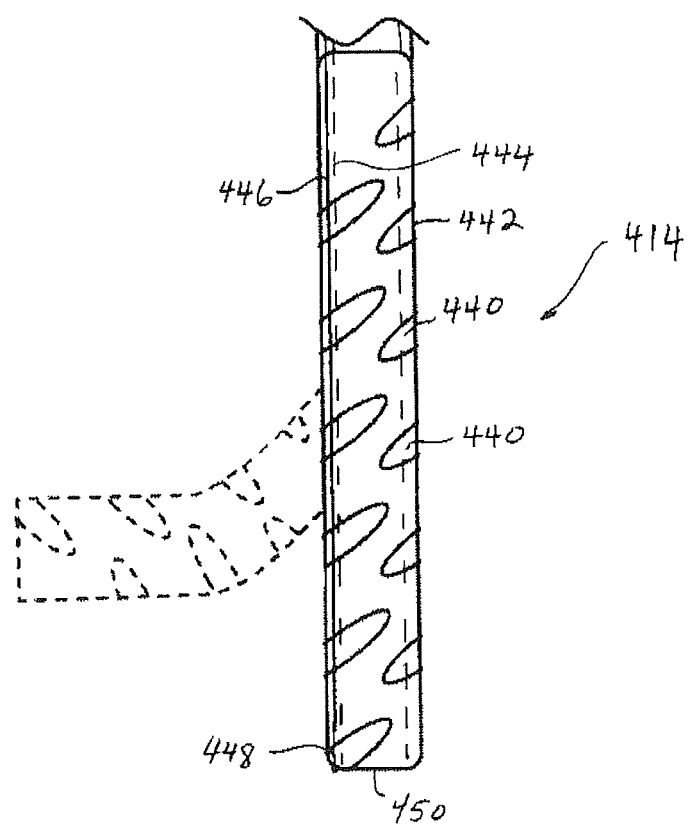
FIG. 37 is an enlarged schematic view of the preshaped port shown in non-actuated and actuated (broken line) configurations.

Turning now to FIGS. 36 through 37, another embodiment of an access system 410 according to the invention is shown. The access system 410 includes an overtube 412, a preshaped port 414 coupled at a distal end of the overtube (distal of cuff 424), and a handle 420 at a proximal end of the overtube 412. The overtube 412 includes a gastric wall securing system, preferably as described with respect to access system 10, i.e. with cuffs 422, 424 expandable via injection ports 426, 428 at the handle 420.

As shown in FIGS. 36 and 37, the preshaped port 414 is configured from a preferably unitary tubular element and most preferably an extruded polymeric tube. Breaks, cuts or superficial recesses 440 are provided along the tube to provide flexibility. A silicone lining 442 covers both the outer surface of the tube to prevent tissue from catching in the breaks. A silicone lining 444 may also be provided to the inner surface of the tube to provide a smooth lumen for endoscope passage. One or more control elements 446, e.g., wires or cables, pass through respective conduits within the tube wall. Each control element 446 has a distal end 448 coupled at a distal portion 450 of the tube 414 and a proximal end that is coupled to an actuator, such as knob 452 on the handle 420. When the actuator 452 is operated, the associated control element 446 is tensioned to cause the tube 414 to bend, e.g., up to 180°, along the breaks and to assume a preshape configuration as shown in broken lines in FIG. 36A. The preshaped port 414 can be maintained in such preshaped configuration to orient an endoscope inserted through the overtube toward a target tissue. If more than one control element is provided within the access system for actuation of the preshaped port (e.g., three control elements), more complex directional control of the preshaped port 414 can be provided. It is appreciated that additional actuators can be provided for each such control element. If necessary to reconfigure the access port or at the conclusion of the procedure, the handle 420 can be operated to release the tension on the control element(s) 446 and straighten the preshaped port 414 to aid in reconfiguring or withdrawing the access system 410 from the patient.

It is appreciated that because the preshaped port 414 is operator manipulatable while within the patient's body, it has steerability that is not provided with access system 10. Thus, while the use of access system 410 in a surgical procedure is generally similar to access system 10, the integration of preshaped port 414 with overtube 412 permits some differences.

Figure 38:
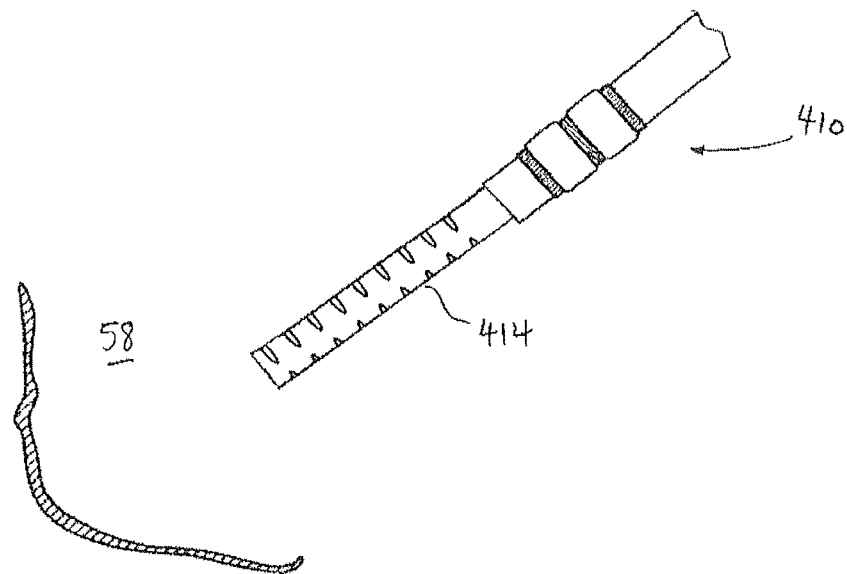
FIGS. 38 through 47 illustrate a method of securing the access system of FIG. 36 within the stomach wall to access the peritoneal cavity.
Figure 39:
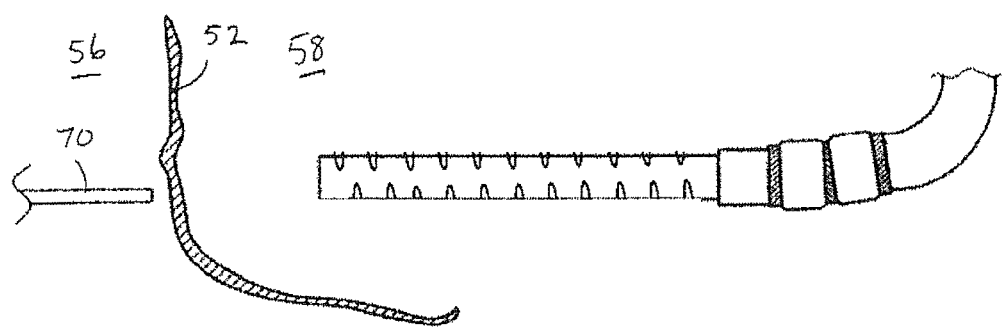
Figure 40:
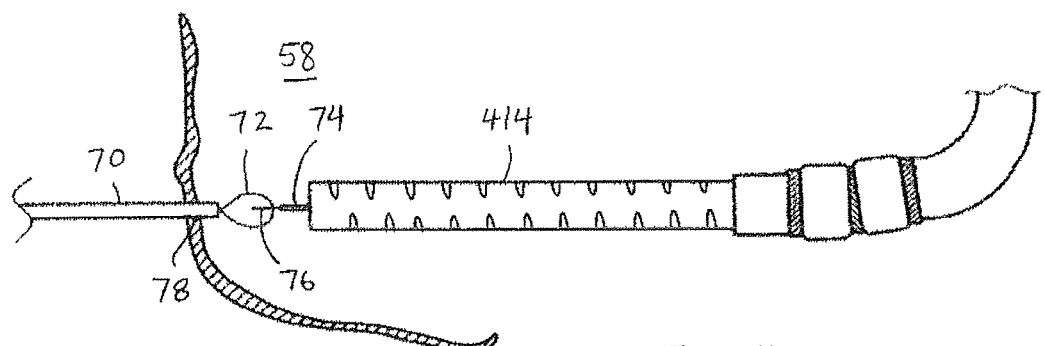
Figure 41:
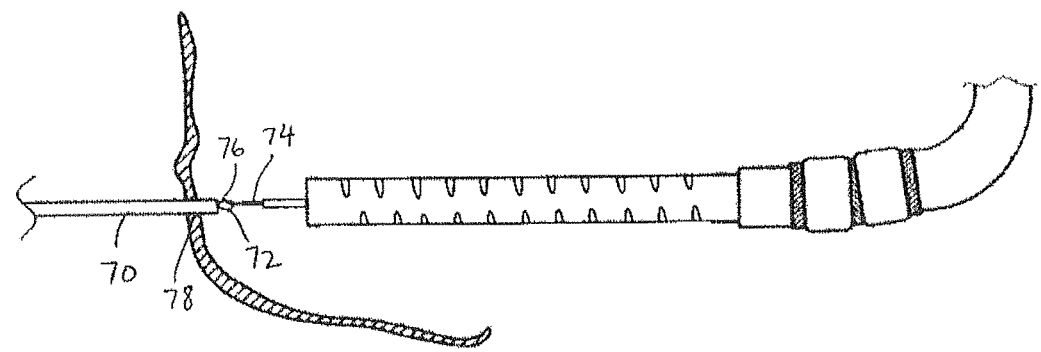

As such, turning now to FIGS. 38 through 47, variations in a surgical procedure with access system 410 relative to the procedure previously described with access system 10 are now described. The access system 410 is introduced into the stomach and advanced adjacent the stomach wall (FIG. 38). An endoscope (not shown) is preferably used within the access system 410 for visualization, but the endoscope for this portion of the procedure is not required to be steerable, as the preshaped port 414 can be actuated to steer the assembly. In accord with an embodiment of the method, a piercing catheter 70 is inserted into the patient's peritoneal cavity 56 from outside the stomach wall 52, pierced through the stomach wall 52, and introduced into the stomach 58 (FIGS. 39 and 40). A snare device 72 is introduced through the piercing catheter 70 and into the stomach 58. A balloon catheter 74 fixed along a guidewire 76 is introduced into the stomach 58 through the preshaped port 414 (FIG. 41).

Figure 42:
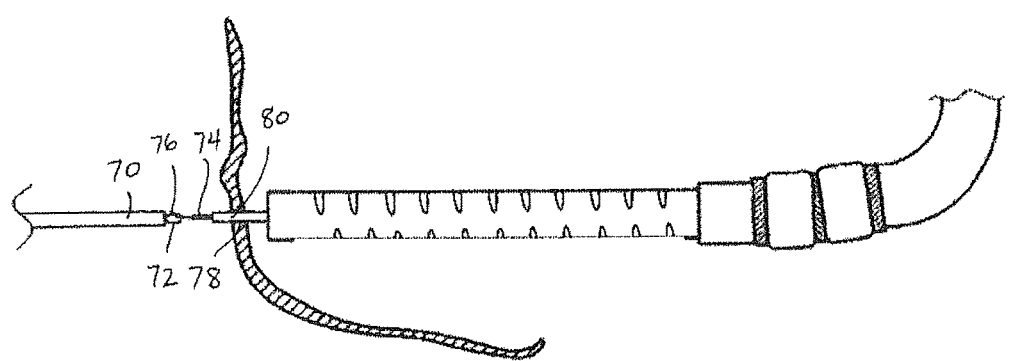
Figure 43:
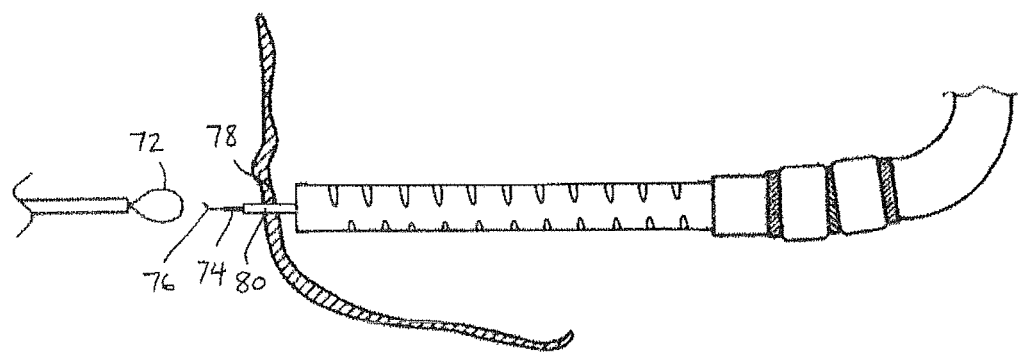

The snare device 72 and cutting instrument 70 are operated to grasp the guidewire 76 and/or balloon catheter 74, and pull the balloon catheter 74 through the piercing 78 in the stomach wall 52 (FIGS. 41 and 42). Once the balloon 80 on the balloon catheter 74 is positioned within the piercing 78, the snare device 72 releases the guidewire 76 and/or balloon catheter 74 so as to decouple the snare device 72 from the balloon catheter 74, as shown in FIG. 43.

Alternatively, the cutting instrument can be advanced through the access system and preshaped port thereof to define a piercing 78 in the stomach wall 52 from the interior of the stomach. The guidewire 76 and balloon catheter 74 are then advanced through the piercing to position the balloon 80 within the piercing 78.

Figure 44:
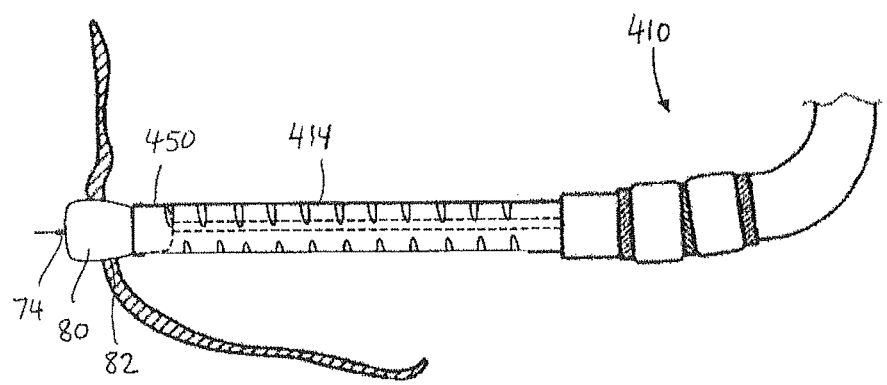
Figure 45:
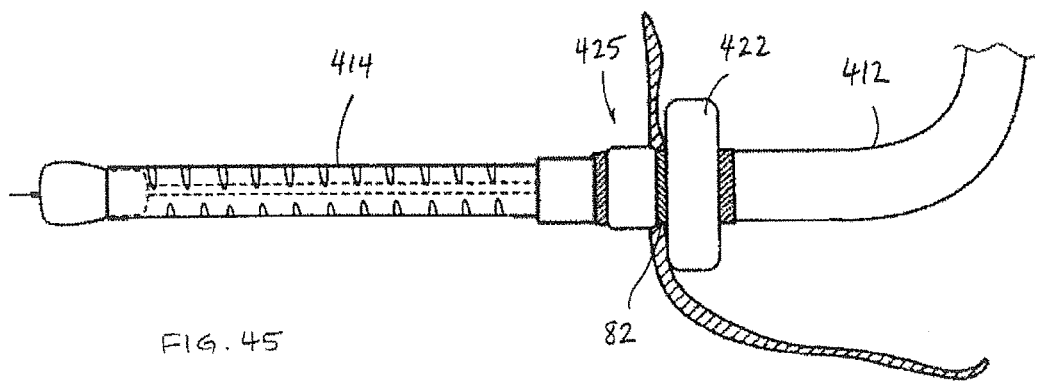
Figure 46:
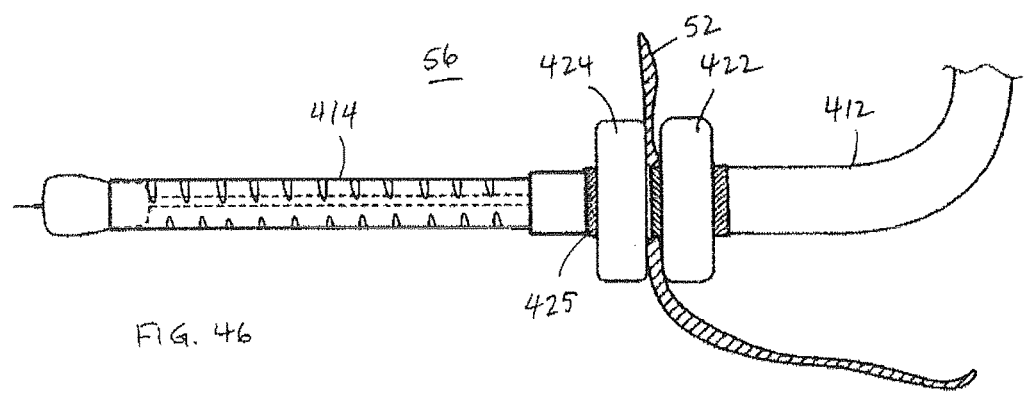

Then, once the balloon 80 is situated within the piercing, the balloon is expanded upon activation from outside the patient by pressurizing a fluid through the balloon catheter 74. The balloon 80 can be located partially inside the distal end 450 of the preshaped port 414 or completely external the distal end of the port. As the balloon 80 is expanded, the piercing is dilated to create a hole 82 of sufficient size to receive the preshaped port 414 of the access system 410 (FIG. 44). The port 414 is advanced through the hole 82 and then the distal end 425 of the overtube 412 is advanced up to the proximal cuff 422, which is expanded (FIG. 45). Then the distal cuff 424 is expanded to secure the access system to the stomach wall 52 at the distal end 425 of the overtube 412 to the between the proximal and distal cuffs 422, 424 with the preshaped port 414 extending within the peritoneal cavity 56 (FIG. 46).

Figure 47:
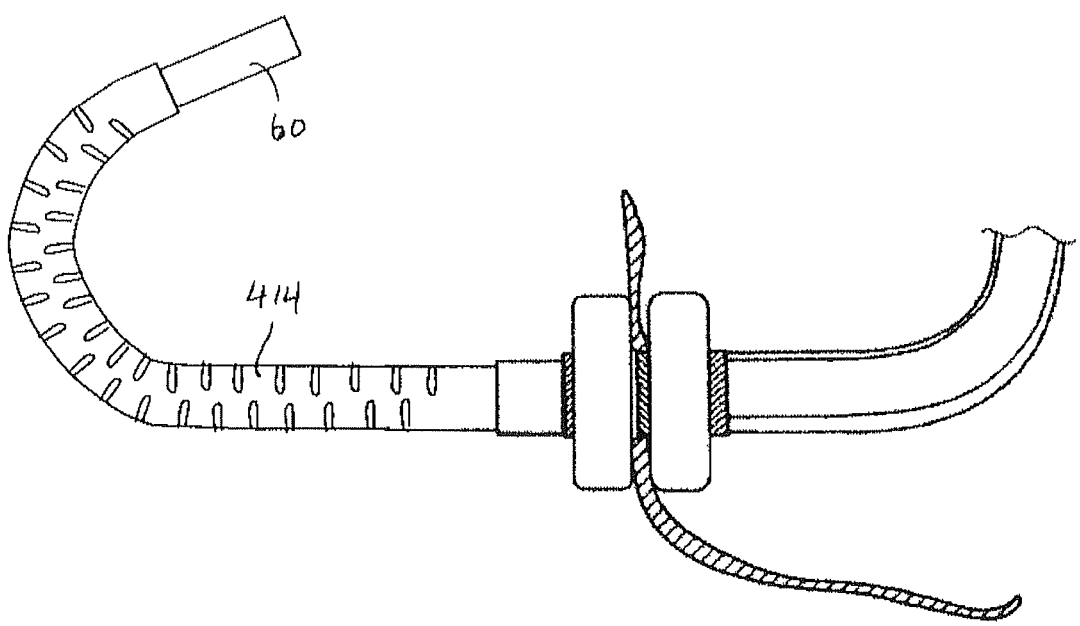

The balloon 80 is deflated, and the balloon catheter 74 and guide 76 are withdrawn from the access system 410. The preshaped port 414 is then actuated from the handle 420 (FIGS. 36 and 38) to cause the port to assume a curved or bent configuration. An endoscope 60 and other instruments are then advanced through the port 414 and directed to pertinent tissue, as previously described, for performing and concluding a surgical procedure on tissue within the peritoneal cavity (FIG. 47).

Referring now to FIGS. 48 and 48A, another embodiment of an access system 710 is shown. The system includes an overtube 712, as described above with respect to overtube 12, and a port 714. Port 714 includes a tubular member 742 having a proximal end defining multiple lumen 743a, 743b. The distal end of port 714 divides at a Y to include a plurality of pre-shaped tubular distal portions 744a, 744b, each similar to pre-shaped distal portion 44. Each distal portion 744a, 744b is preferably associated with one of lumen 743a, 743b. Each of the pre-shaped distal portions 744a, 744b can be provided with a different shape to direct instruments positioned therethrough toward anatomical structure.

Figure 49:
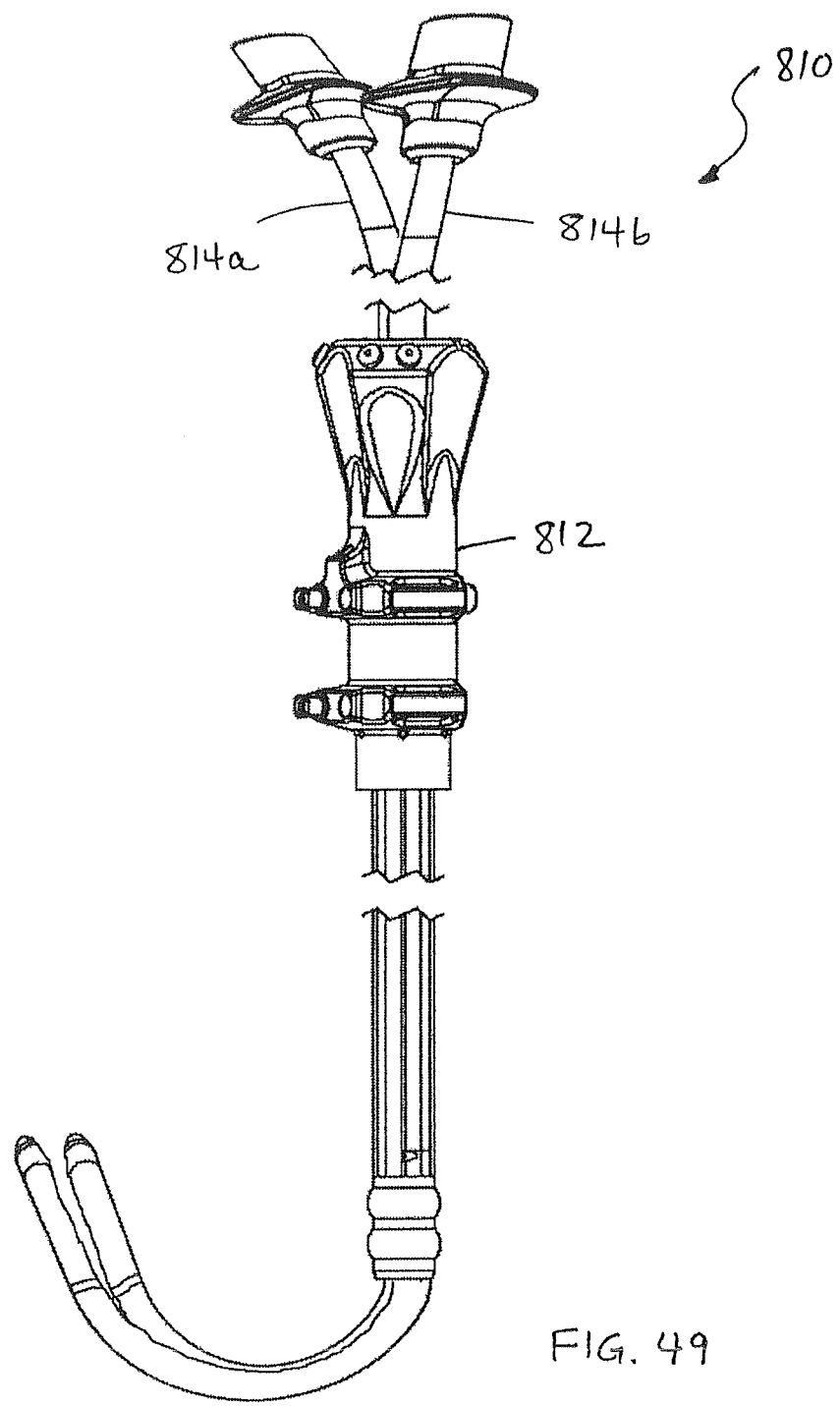
FIG. 49 is broken side elevation view of a fourth embodiment of an access system according to the invention.

Turning now to FIG. 49, another embodiment of an access system 810 is shown. The system includes an overtube 812, as described above with respect to overtube 12, and a plurality of ports 814a, 814b positionable therethrough. Each port 814a, 814b is generally similar to port 14, through smaller in diameter to permit the multiple ports to be received within the overtube 812 at once.

Figure 50:
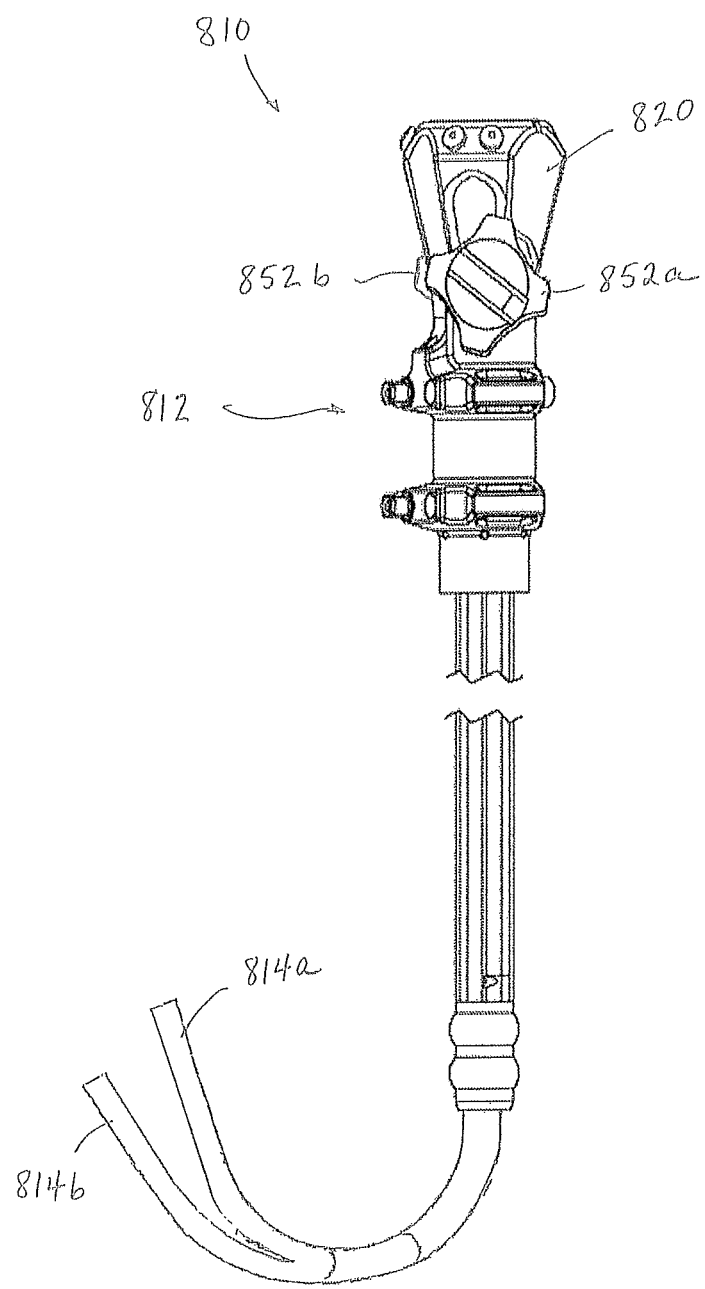
FIG. 50 is broken side elevation view of a fifth embodiment of an access system according to the invention.

Referring now to FIG. 50, another embodiment of an access system 910 is shown. The system includes an overtube 812 with a plurality of preshaped port 814a, 814b coupled at a distal end of the overtube, and a handle 820 at a proximal end of the overtube 812. The arrangement of system 810 is similar to system 410, with multiple ports at the distal end of the overtube. The handle includes two actuators 852a, 852b, to apply and release tension on control elements extending from the handle to the distal end of the respective ports to control shaping of the ports 814a, 814b into respective predetermined shapes.

Figure 51:
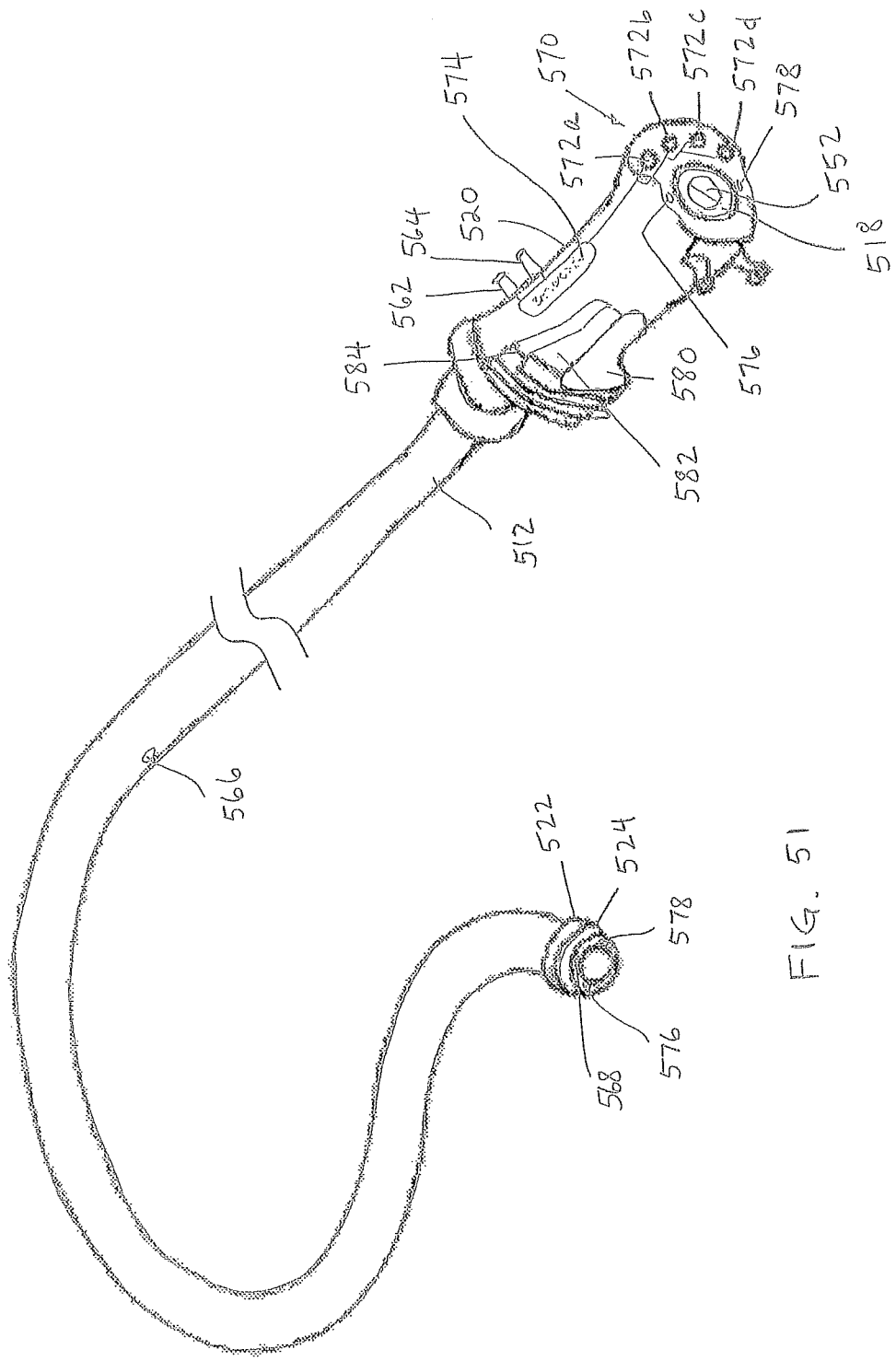
FIG. 51 is a broken perspective view of a sixth embodiment of an access system according to the invention.
Figure 52:
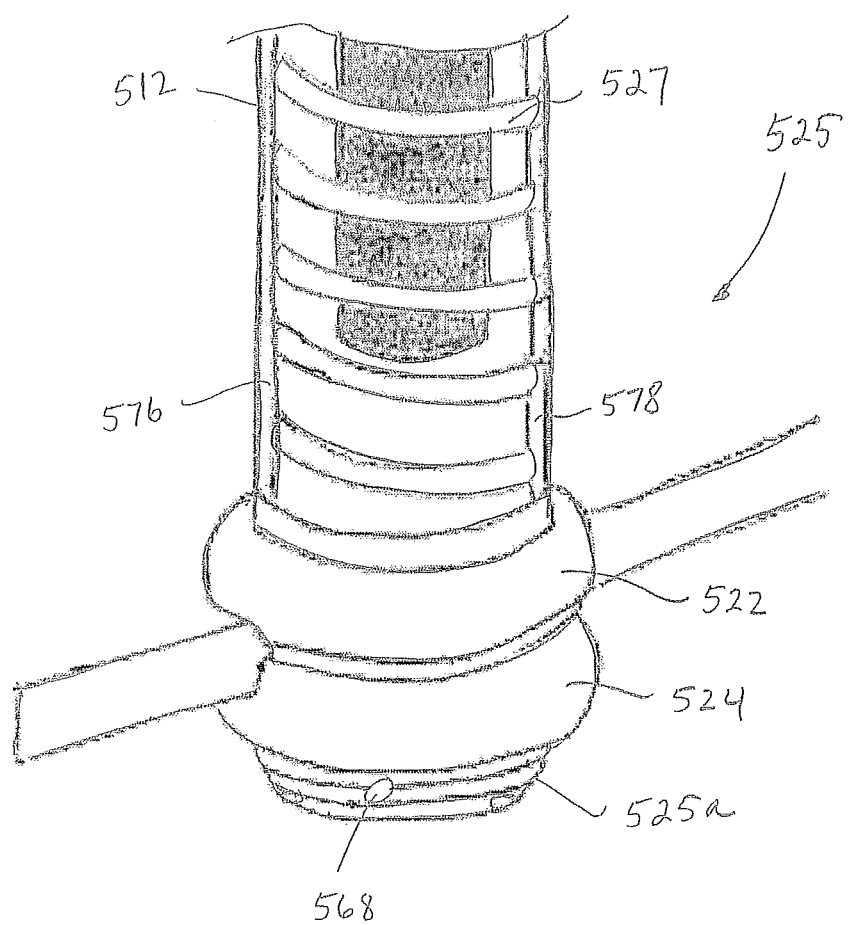
FIG. 52 is a enlarged broken perspective view of sixth embodiment of the access system coupled to the stomach wall to access the peritoneal cavity.

Turning now to FIGS. 51 and 52, another embodiment of an access system 510 according to the invention is shown. The access system includes an overtube 512 and a proximal handle 520. The overtube 512 is provided with a gastric wall securing system preferably as described above, i.e., with expandable proximal and distal cuffs 522, 524 adjacent its distal end 525 and the requisite structural and functional elements to effect such expansion and contraction. The distal tip 525a is tapered to facilitate driving insertion through the anatomical passageway and through the hole created in the stomach wall, as previously described above according to the method. In addition, the overtube 512 includes a coil reinforcement 527 for lateral wall support. The overtube 512 may be used with or integrated with a preshaped port, as described above. According to aspects of access system 510, the access system is provided with a system (means) for insufflating/deflating the peritoneal space separately from the gastric space, and a closure system (means) integrated into the access system to close the hole made in the intragastric wall in which the access system is secured to seal the hole after the access system has been removed from the hole. Either of such systems (means) may be individually provided in any access system in accord with the invention.

Referring to FIGS. 51 and 52, the system to control insufflation/deflation includes a seal and/or valve, collectively 560 and first and second ports 562, 564 extending at least partially through the overtube. The seal/valve 560 is preferably a self-sealing valve 560 within the lumen 518 of the overtube 512 (e.g., at the handle). The first port 562 is a pressure controlled port extending from the handle 520 to an exit location 566 intermediate the handle 520 and the proximal cuff 522. The second port 564 is a pressure controlled port extending from the handle 520 to an exit location 568 at or distal the distal cuff 524. The handle 520 is also provided with a pressure control system 570 to inject or evacuate air through the respective first and second ports 562, 564. For example, control system 570 may include buttons 572a-d to activate injection or evacuation of air through each of the first and second ports 562, 564 (four buttons 572a-d). The pressure control system 570 preferably also includes monitoring system 574 to monitor the pressure in at least one of, and preferably both of, the stomach and the peritoneal cavity, and to provide feedback of such pressure(s) to the access system operator.

In use, once the access system has been secured to the stomach wall to separate the intragastric space from the peritoneal space, the pressures in the peritoneal space and stomach can be separately controlled. With the access system so secured, the first port exit 566 lies within the stomach and the second port exit 568 is located within the peritoneal cavity. In addition, the esophageal sphincter forms a relatively air tight seal about the exterior of the overtube 512. Air can then be evacuated from first port 562, to reduce air pressure within the stomach, while air can be injected to or maintained within the peritoneal cavity to increase or maintain peritoneal pressure. The result will be that the stomach will collapse to increase visibility at the surgical site. Later, peritoneal air pressure can be decreased if desired or the stomach air pressure can be increased as desired.

In addition, the access system 510 includes a closure system that facilitates rapid closure of the hole 82 in the stomach wall 52 after removal of the overtube from the hole. (See, e.g., FIG. 17.) According to an exemplar embodiment, the closure system generally includes a needle deployment and retraction system, a tissue fastener deployment system able to deploy fasteners through needles deployed in tissue, and a cinching mechanism adapted to cinch the proximal ends of multiple tissue fasteners together to close the hole in the tissue, as described hereinafter. The various systems are preferably actuatable from discrete or integrated actuators, e.g., levers 580, 582, 584 on the handle 520, or instruments coupled to the handle or inserted through peripheral lumen 576, 578 exterior to the central lumen 518 of the overtube 512. The actuators operate control members to operate effectors to advance, retract, deploy and cinch, as required. The actuators are coupled to control members required for such operations can be those described in U.S. Pat. No. 6,824,548, U.S. Pub. No. 20040249395, U.S. Pub. No. 20050261708, U.S. Pub. No. 20060004409 and/or U.S. Pub. No. US2006/0004410 which are hereby incorporated by reference herein in their entireties. Such patent and publications describe flexible endoscopic instruments adapted to provide significant pushing force at their distal ends, and the mechanisms therein can be incorporated into the access system to advance (and retract) one or more needles and fasteners in the manner now described. In general, the actuators (e.g., levers) are preferably coupled to the effectors (e.g. needle, push rod) in a simple mechanical arrangement such that depression of a particular lever causes the axial movement of the respective effector. For instance a first actuator coupled to a needle may be actuated to extend the needle from a lumen of the overtube to thereby pierce tissue. A second actuator coupled to a pushrod, which is coaxially positioned within the lumen of the needle, may be actuated to advance the push rod axially within the needle lumen.

Figure 53:
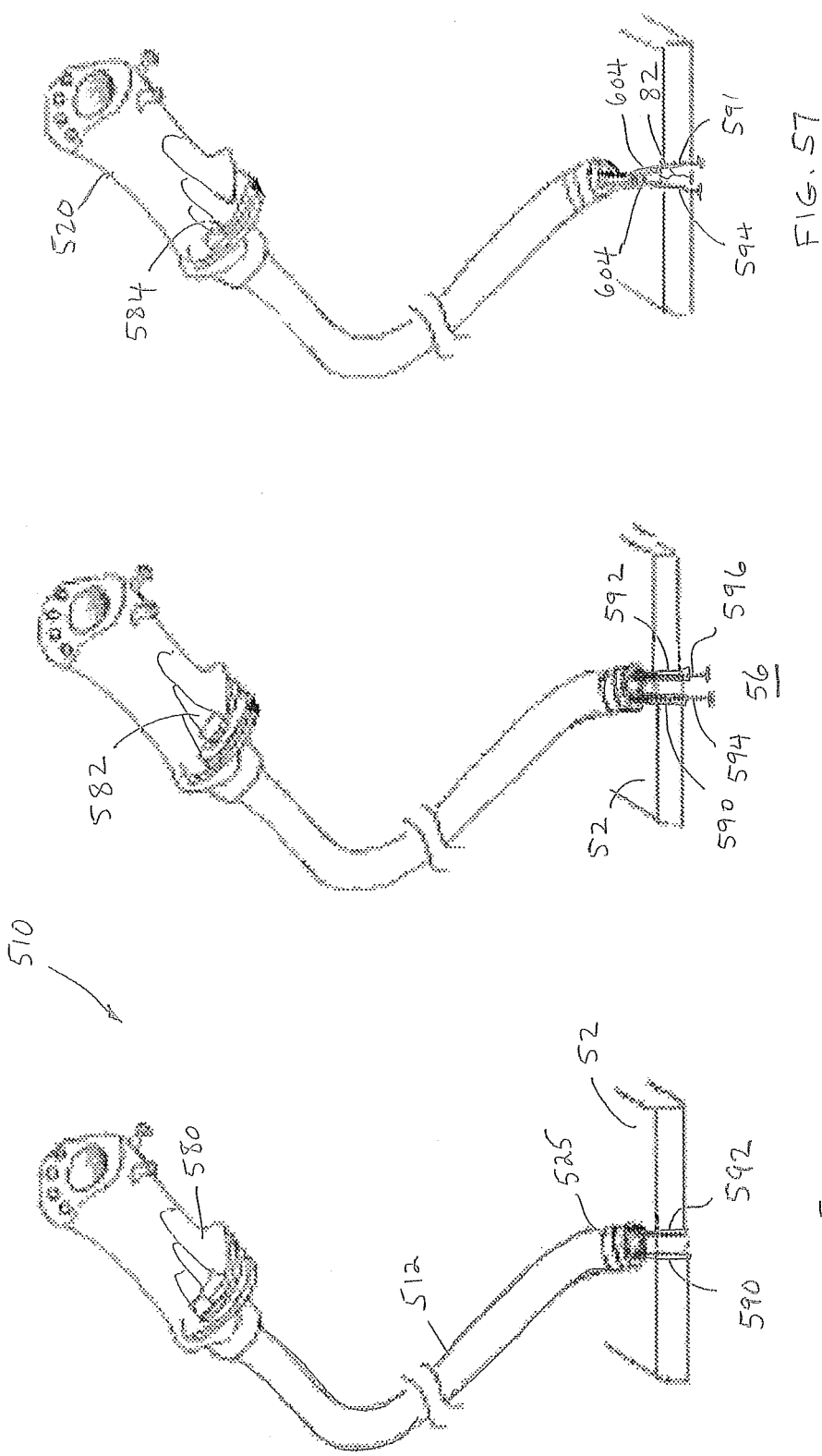
FIG. 53 illustrates the access system being used to deploy hollow needles into the stomach wall.
Figure 54:
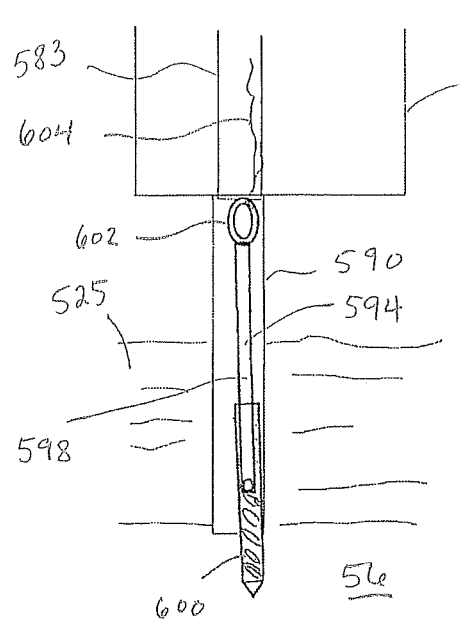
FIG. 54 illustrates a T-shaped fasteners in a collapsed configuration being forced through a needle into the opposite side of the stomach wall.
Figure 56:
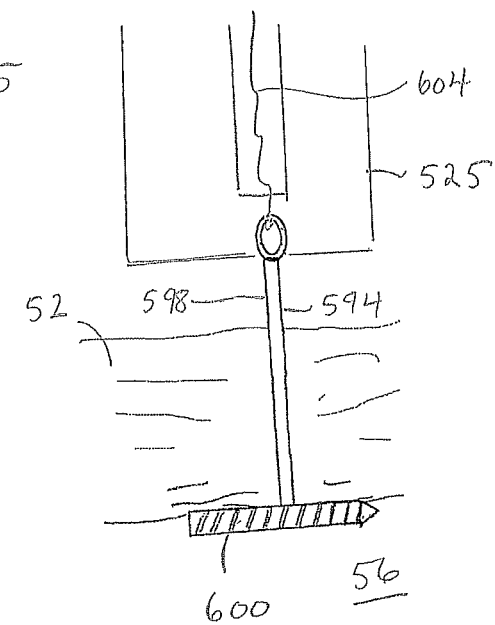
FIG. 56 illustrates the T-shaped fasteners deployed within the stomach wall and the hollow needles retracted within the access system.

More particularly, referring to FIGS. 53 and 54, the access system 510 includes at least one extendable hollow needle, and preferably a plurality of extendable hollow needles 590, 592 from its distal end 525. The needles 590, 592 are initially retracted within the distal end 525 of the access system 510. Upon actuation of an associated actuator 580, the needles 590, 592 are extended from the distal end 525. As shown, the needles 590, 592 can then be pierced through the stomach wall 52. This step is done prior to any hole formation in the stomach wall 52 of sufficient size to permit passage of the distal end 525 of overtube 512. It is appreciated that a piercing instrument and grasper may optionally be inserted from the peritoneal cavity into the stomach may be used in conjunction with the access system to stabilize the distal end 525 during needle insertion.

Referring to FIGS. 54 and 55, after the needles 590, 592 have been inserted into the stomach wall 52 and while such needles are within the stomach wall, the appropriate actuator 582 is manipulated to axially advance a push rod 583 positioned within the needle lumen to deploy fasteners 594, 596 through the needles 590, 592 so as to have a portion which extends through to the other side of the stomach wall (within the peritoneal cavity 56). According to a preferred aspect of the invention, the fasteners 594 are T-shaped tags (in a deployed configuration) having a shaft 598 with a head 600 transverse to the shaft at one end, and an eye 602 or other suture engaging structure at the other end. Suture material 604 is coupled to the eye 602. The tag 594 (as shown in FIG. 54) is collapsible into a pre-deployed configuration within each needle, with the head 600 substantially parallel to the shaft 598 and preferably retained within the needles (although the distal end of the head may extend from the needle). Upon deployment, the tag 594 is forced out of the needle, head 600 first, through the stomach wall (and onto the peritoneal side of the stomach wall), while the shaft extends within the tissue and the suture material 604 remains coupled to the access system. The tag 594 may assume a T-shape after deployment by an inherent bias between the head 600 and shaft 598, or by retraction of the shaft 598 relative to the head 600. T-shaped tags 594 of this design are described in detail in previously incorporated U.S. Ser. No. 12/030,244. Other tag configurations or fasteners could also be used. For example one alternate tag configuration may be a modification of tag 594 in which shaft 598 is formed entirely of suture material and coupled directly to a mid portion of head 600. Multiple fasteners 594, 596 may be deployed at once through multiple needles 590, 592 provided to the access system 510. Alternatively, where the access system includes a single needle, individual fasteners may be deployed sequentially using a single needle with a store of fasteners, with the access system rotated between deployments for polar displacement of the fasteners about a subsequent hole for the distal end 525. After the fasteners have been deployed, a procedure through the stomach wall is performed as described above. Referring to FIG. 57, at the conclusion of the procedure, once the access system is withdrawn from a hole in the stomach wall, the third actuator 584 on the handle 520 is operated to pull on the suture material 604 and cinch the fasteners 594, 596 together about the hole 82 to close the hole. The T-shaped tag provides a small profile aiding deployment and provides strong resistance to pull-out during cinching. The suture material 604 of the fasteners is then clipped, knotted or otherwise secured to maintain closure of the hole. Preferably a cinch delivery assembly is used to grasp the suture connecting the T-tags and pull the suture lines within the cinch while drawing the T-tags and associated tissue into close apposition thereby closing a hole. The cinch preferably contains a one way mechanism such that the suture lines may be drawn taught and not allow them to loosen. Various cinch designs such as those described in U.S. Pat. App. Pub. Nos. 20040249395, 20050261708 and 20060004409 are suitable for performing the closure operation.

There have been described and illustrated herein several embodiments of an access system and methods of performing intra-abdominal surgery. While particular embodiments of the invention have been described, it is not intended that the invention be limited thereto, as it is intended that the invention be as broad in scope as the art will allow and that the specification be read likewise. Thus, while a particular gastric wall securing system has been disclosed, it will be appreciated that other gastric wall securing system can be used as well, including mechanically expandable systems. In addition, while particular types of instruments for the cutting and piercing tissue, and drawing a balloon from the stomach cavity to within the stomach wall have been disclosed, it will be understood that other suitable instruments can be used as well. Also, while a preferred system of tunneling and dissection balloons has been disclosed for separation of the tissues within the abdomen, it will be recognized that other tissue tunneling and/or dissection instruments can be used instead. Furthermore, while an exemplar mechanism for operating the closure system has been disclosed, it is understood that other suitable mechanism and handles for operation thereof can be similarly used. Moreover, while a T-shaped tag is preferred for effecting closure of a hole through which the access system is inserted, it is appreciated that other suitable fasteners can be used as well. In addition, while the access system has been described with respect to providing access from the intragastric space to the peritoneal cavity through the stomach, it can likewise be used through the anus and colon. Moreover, it can also be used as an access system into the peritoneal space through the vagina. It will therefore be appreciated by those skilled in the art that yet other modifications could be made to the provided invention without deviating from its spirit and scope as claimed.

What is claimed is:

1. A method of intra-abdominal surgery, comprising:
   a) inserting a distal end of a natural orifice transluminal endoscopic surgery (NOTES) access system into a hole in an anatomic wall, the access system having an overtube with a distal end;
   b) securing the access system to the anatomic wall at the hole;
   c) inserting a flexible port through the overtube of the access system, the port having a shaped portion at the distal end of the overtube;
   d) inserting a flexible endoscope through the port;
   e) using the shaped portion of the flexible port to direct the flexible endoscope along a determined trajectory, the endoscope extending through the port;
   f) inserting a flexible tunneling instrument through the port and longitudinally expanding a distal end of the tunneling instrument to form a tunnel at an interface between first and second tissues; and
   g) inserting a dissecting instrument into the tunnel and radially expanding the dissecting instrument within the tunnel at the interface between first and second tissues to cause dissection of the first and second tissues from each other.

2. A method according to claim 1, further comprising:
before inserting the access system into the hole in the anatomic wall,
   i) making a piercing through the anatomic wall,
   ii) inserting a balloon into the piercing; and
   iii) expanding the balloon to dilate the piercing and define the hole in the anatomic wall.

3. A method according to claim 2, wherein:
the anatomic wall is the vaginal wall.

4. A method according to claim 2, wherein:
the anatomic wall is a wall of intragastric system.

5. A method according to claim 4, wherein:
the anatomic wall is the stomach wall.

6. A method according to claim 5, wherein:
said making a piercing includes piercing the stomach wall from an exterior of the intragastric space to the interior of the intragastric space.

7. A method according to claim 5, wherein:
said making a piercing includes piercing the gastric wall from an interior of the intragastric space to the exterior of the intragastric space.

8. A method according to claim 1, wherein:
at least one of the tunneling instrument and the dissecting instrument includes a balloon which upon expansion tunnels and/or dissects.

9. A method according to claim 1, wherein:
the dissecting instrument and tunneling instrument are integrated into a single instrument.

10. A method according to claim 1, wherein:
the first tissue is the gallbladder and the second tissue is the liver.

11. A method according to claim 1, further comprising:
inserting a multilumen device through said port; and
inserting instruments through a plurality of lumen of said multilumen device.

12. A method according to claim 1, wherein:
the access system has a proximal handle, and the port is removable from said overtube at the handle.

13. A method according to claim 1, wherein:
changing the shape of the shape portion of the port before the endoscope is within the port but while the port is within the patient.

14. A method according to claim 1, further comprising:
changing the shape of the shape portion of the port while the endoscope is within the port.

* * * * *